(12) United States Patent
Aoki et al.

(10) Patent No.: US 9,955,899 B2
(45) Date of Patent: May 1, 2018

(54) RESPIRATORY WAVEFORM ANALYZER

(75) Inventors: Toshiki Aoki, Tokyo (JP); Hidetoshi Dainobu, Tokyo (JP); Teiji Ukawa, Tokyo (JP); Masahiro Echigo, Tokyo (JP)

(73) Assignee: NIHON KOHDEN CORPORATION, Tokyo (JP)

(*) Notice: Subject to any disclaimer, the term of this patent is extended or adjusted under 35 U.S.C. 154(b) by 1620 days.

(21) Appl. No.: 12/749,607

(22) Filed: Mar. 30, 2010

(65) Prior Publication Data

US 2010/0249631 A1  Sep. 30, 2010

(30) Foreign Application Priority Data

Mar. 30, 2009  (JP) ................. 2009-082039

(51) Int. Cl.
*A61B 5/02* (2006.01)
*A61B 5/083* (2006.01)
*G01N 21/3504* (2014.01)
*A61B 5/00* (2006.01)
*G01N 33/497* (2006.01)

(52) U.S. Cl.
CPC .......... *A61B 5/0836* (2013.01); *A61B 5/7221* (2013.01); *G01N 21/3504* (2013.01); *A61B 5/7203* (2013.01); *A61B 5/746* (2013.01); *G01N 33/497* (2013.01)

(58) Field of Classification Search
CPC ....... A61B 5/0836; A61B 5/097; A61B 5/083; A61B 5/085; A61B 5/1135; A61B 5/113; A61B 5/0809; A61B 5/0878; A61B 5/087; A61B 5/09; A61B 5/0871; A61B 5/093; A61B 5/095; A61B 7/003

USPC .................................................. 600/529–543
See application file for complete search history.

(56) References Cited

U.S. PATENT DOCUMENTS

| 4,390,869 A | 6/1983 | Christen et al. |
| 4,648,396 A | 3/1987 | Raemer |
| 4,651,746 A * | 3/1987 | Wall .............................. 600/483 |
| 5,003,985 A * | 4/1991 | White et al. ................... 600/529 |
| 5,140,981 A * | 8/1992 | Lindstrom ............... 128/203.25 |

(Continued)

FOREIGN PATENT DOCUMENTS

JP   2003-532442 A   11/2003

OTHER PUBLICATIONS

Office Action dated Oct. 15, 2012 issued by the Japanese Patent Office in counterpart Japanese Application No. 2009-082039.

(Continued)

*Primary Examiner* — Patricia Mallari
*Assistant Examiner* — Vasuda Ramachandran
(74) *Attorney, Agent, or Firm* — Sughrue Mion, PLLC

(57) ABSTRACT

A respiratory waveform analyzer, operable to analyze a respiratory waveform, which is generated based on a temporal change of a concentration of a component in respiratory gas of a subject, includes: a respiratory gas concentration generator which generates a concentration signal based on an output signal from a sensor that is placed to measure the concentration of the component; a flatness calculator which calculates a flatness indicative of flat degree of the respiratory waveform based on a temporal change of the concentration signal; and a reliability calculator which calculates a reliability of the respiratory waveform based on the flatness and the concentration signal.

15 Claims, 20 Drawing Sheets

(56) References Cited

U.S. PATENT DOCUMENTS

| | | | |
|---|---|---|---|
| 5,386,833 A | | 2/1995 | Uhen |
| 5,445,160 A | * | 8/1995 | Culver et al. ................. 600/532 |
| 5,965,887 A | | 10/1999 | Patton |
| 6,428,483 B1 | * | 8/2002 | Carlebach .................... 600/532 |
| 2008/0119753 A1 | * | 5/2008 | Ricciardelli et al. ......... 600/532 |

OTHER PUBLICATIONS

European Search Report dated Nov. 20, 2012 issued by the European Patent Office in corresponding European Patent Application No. 10158368.0.
Search Report dated Feb. 28, 2013, issued by the European Patent Office in counterpart European Patent Application No. 10158368.0.
Office Action dated May 24, 2013 issued by the Japanese Patent Office in counterpart Japanese Application No. 2009-082039.
Office Action dated Oct. 12, 2015, issued by the European Patent Office in counterpart European Application No. 10158368.0.

* cited by examiner

RESPIRATORY WAVEFORM ANALYZER

BACKGROUND OF THE INVENTION

The present invention relates to a respiratory waveform analyzer, and more particularly to a respiratory waveform analyzer which analyzes the respiratory waveform by detecting the concentration of a component in respiratory gas of the subject.

Various apparatuses and methods of monitoring the respiration of the patient who must undergo respiratory management in clinical practice or the like have been proposed. For example, the method which is called capnometry is known as a method in which a temporal change of the partial pressure of carbon dioxide contained in the expiration or the like, i.e., the concentration of carbon dioxide ($CO_2$ concentration) in the expiration is measured to know the respiratory condition of the patient (for example, see JP-A-2003-532442).

As a method of measuring the $CO_2$ concentration in the expiration of the patient, the photoacoustic spectroscopy, the mass spectroscopy, the Raman scattering spectroscopy, and infrared absorption spectroscopy (IR spectroscopy), and the like are known. Among them, the IR spectroscopy is known as a method in which expiratory gas of the patient is irradiated with light having the carbon dioxide absorption property, such as infrared light, transmitted or reflected light is detected, and the $CO_2$ concentration in the expiration is measured from the absorption rate of the infrared light by the expiratory gas.

In a related-art capnometry, in the waveform of the $CO_2$ concentration in the expiration, the maximum value of the waveform corresponding to one respiration of the patient is set as the effective concentration of the respiration, and detected as an end-tidal carbon dioxide concentration (ETCO2). In the case where the $CO_2$ concentration in the expiration is measured by using the above-described IR spectroscopy, particularly, the problem is to improve the accuracy of detecting the ETCO2.

When the $CO_2$ concentration in the expiration is measured by using an expiratory gas sensor of the mainstream type which is connected to a respiratory circuit to measure the $CO_2$ concentration, for example, the inspiration of the patient is sometimes humidified. In such a case, it is often that water such as dew condensation water is reserved in the respiratory circuit. When such water is attached to a light irradiation portion or detection portion of the expiratory gas sensor in the respiratory circuit, the $CO_2$ concentration cannot be correctly detected, with the result that the incorrectly detected concentration appears as noise components in the measured waveform. Then, it is often that a peak of such noise components is falsely detected as the ETCO2.

In the case where only expirations from the patient with respect to the air supply to the patient by a ventilator are to be counted as the respiratory rate, it is difficult to correctly remove the component of spontaneous respiration of the patient from the measured waveform.

SUMMARY

It is therefore an object of the invention to provide a respiratory waveform analyzer which is capable of correctly detecting noise components in a respiratory waveform and analyzing the respiratory waveform with a high accuracy.

In order to achieve the object, according to the invention, there is provided a respiratory waveform analyzer, operable to analyze a respiratory waveform, which is generated based on a temporal change of a concentration of a component in respiratory gas of a subject, the respiratory waveform analyzer comprising:

a respiratory gas concentration generator which generates a concentration signal based on an output signal from a sensor that is placed to measure the concentration of the component;

a flatness calculator which calculates a flatness indicative of flat degree of the respiratory waveform based on a temporal change of the concentration signal; and a reliability calculator which calculates a reliability of the respiratory waveform based on the flatness and the concentration signal.

The flatness may be a function of an accumulated value which is obtained by accumulating degree of a difference in a time interval over a plurality of the time intervals, based on the concentration signal.

The degree of the difference may be an absolute value of the difference.

The degree of the difference may be obtained by raising the difference to the power of the even number.

The reliability calculator may calculate the reliability based on the flatness which is calculated at a timing by the flatness calculator, and the concentration signal at the timing.

The respiratory waveform analyzer may further include an effective concentration detector which detects a value of the concentration signal at a timing when the reliability that is calculated in a predetermined concentration detecting time period is maximum, as an effective concentration in the concentration detecting time period.

The effective concentration detector may accumulate the reliability in the concentration detecting time period to obtain an accumulated value in the concentration detecting time period, and detect the effective concentration in the concentration detecting time period when the accumulated value exceeds a predetermined reliability.

The concentration detecting time period is a time period corresponding to one cycle of the respiratory waveform.

The respiratory waveform analyzer may further include a weighted average processor which, when a plurality of the effective concentrations are detected, weights each of the effective concentrations in accordance with degree of the accumulated value in the corresponding concentration detecting time period, and averages the weighted effective concentrations, to calculate a weighted average value.

The respiratory waveform analyzer may further include a display that displays at least one of a number at which the effective concentration detector detects the effective concentration in a time period, and the weighted average value calculated by the weighted average processor.

The respiratory gas concentration generator may include: a respiratory gas concentration detector which converts the analog output signal from the sensor to a digital respiratory gas signal; and a respiratory gas concentration calculator which generates a respiratory waveform signal based on the respiratory gas signal from the respiratory gas concentration detector. The concentration signal may be the respiratory waveform signal. When a value of the respiratory gas signal is a value or greater, which indicates that the concentration of the component is high, the effective concentration detector may detect the effective concentration in the concentration detecting time period.

The respiratory waveform analyzer may further include a concentration detection value corrector which corrects the respiratory waveform signal corresponding to the respiratory gas signal, in accordance with a ratio of the respiratory gas signal to a predetermined reference value.

The respiratory waveform analyzer may further include: a respiratory airway adaptor in which the respiratory gas of the subject flows; and a liquid detector which detects a liquid in the respiratory airway adaptor.

In order to achieve the object, according to the invention, there is also provided a respiratory waveform analyzer, operable to analyze a respiratory waveform, which is generated based on a temporal change of a concentration of a component in respiratory gas of a subject, the respiratory waveform analyzer comprising:

a respiratory gas concentration detector which converts a analog output signal from a sensor that is placed to detect the concentration of the component, to a digital respiratory gas signal;

a respiratory gas concentration calculator which generates a respiratory waveform signal based on the respiratory gas signal from the respiratory gas concentration detector; and a concentration detection value corrector which corrects the respiratory waveform signal corresponding to the respiratory gas signal, in accordance with a ratio of the respiratory gas signal to a predetermined reference value.

In order to achieve the object, according to the invention, there is also provided a respiratory waveform analyzer, operable to analyze a respiratory waveform, which is generated based on a temporal change of a concentration of a component in respiratory gas of a subject, the respiratory waveform analyzer comprising:

a respiratory airway adaptor in which the respiratory gas of the subject flows, the respiratory airway adaptor provided with a sensor that measures the concentration of the component to output a signal;

a respiratory gas concentration generator which generates a concentration signal based on the signal output by the sensor, the concentration signal indicating degree of the concentration; and a liquid detector which detects a liquid in the respiratory airway adaptor based on the concentration signal.

The liquid detector may compare a value of the concentration signal with at least one preset value and detect the liquid in the respiratory airway adaptor based on comparison result.

The sensor may receive a signal light and a referential light which are different from each other in an absorption property of the component, and the liquid detector may calculate attenuance based on receiving intensities of the signal light and the referential light and detect the liquid in the respiratory airway adaptor based on the attenuance.

The liquid detector may output an attention arousing signal when the comparison result reaches an attention arousal level. The liquid detector may output an alarm signal when the comparison result reaches an alarm level.

The liquid detector may determine that the comparison result reaches the attention arousal level or the alarm level based on one of a difference between the value of the concentration signal and the preset value, number of times at which the value of the concentration signal is larger than the preset value, a time period during which the value of the concentration signal is larger than the present value, number of times at which the value of the concentration signal is smaller than the preset value and a time period during which the value of the concentration signal is smaller than the present value.

The liquid detected by the liquid detector may be a water.

DETAILED DESCRIPTION OF EMBODIMENTS

Hereinafter, the invention will be described through an embodiment of the invention. The invention set forth in the claims is not restricted by the following embodiment. All of the combinations of the features described in the embodiment are not always essential to the solving means of the invention.

Figure 1:
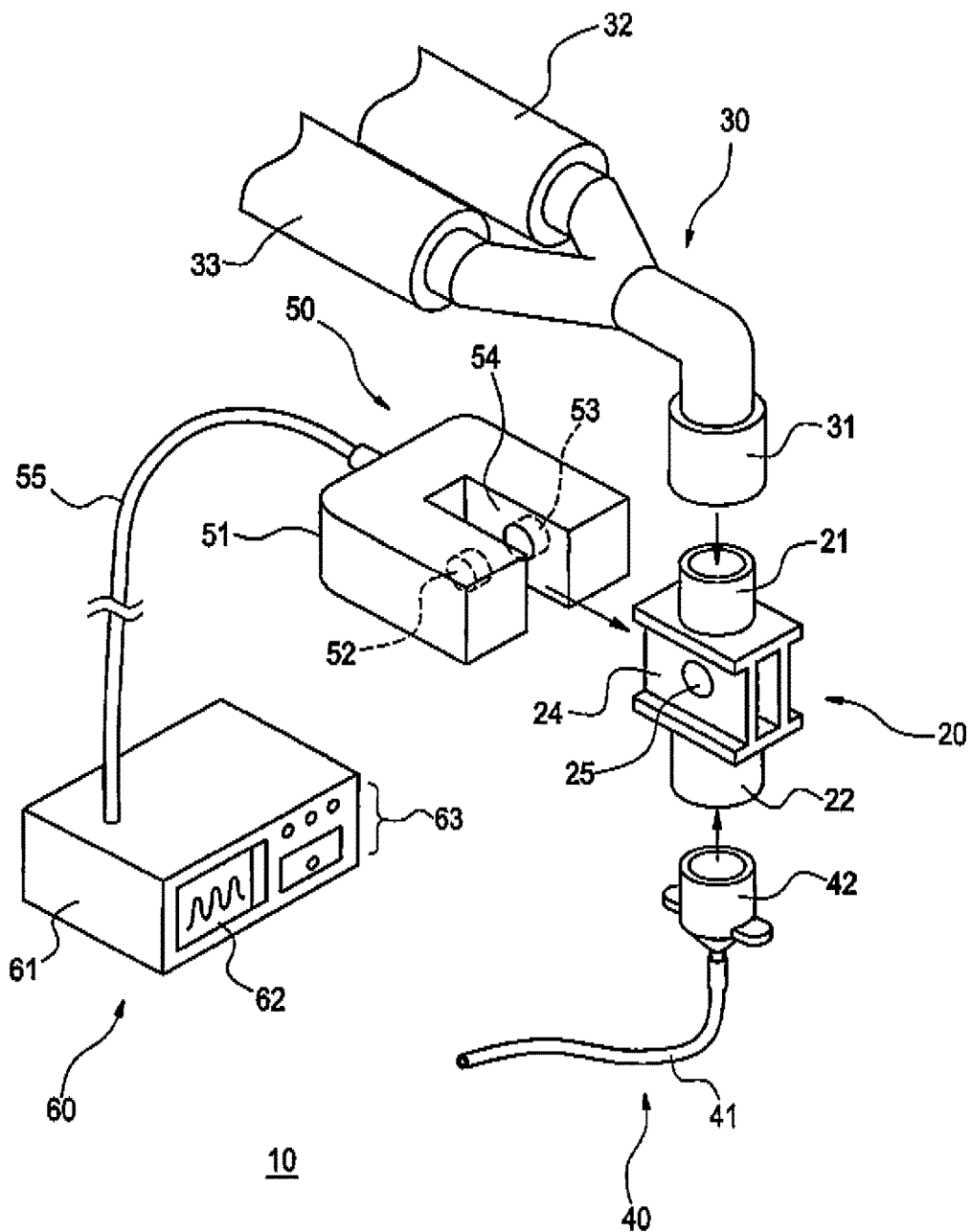
FIG. 1 is an exploded perspective view showing the configuration of a respiratory waveform analyzer of an embodiment.
Figure 2:
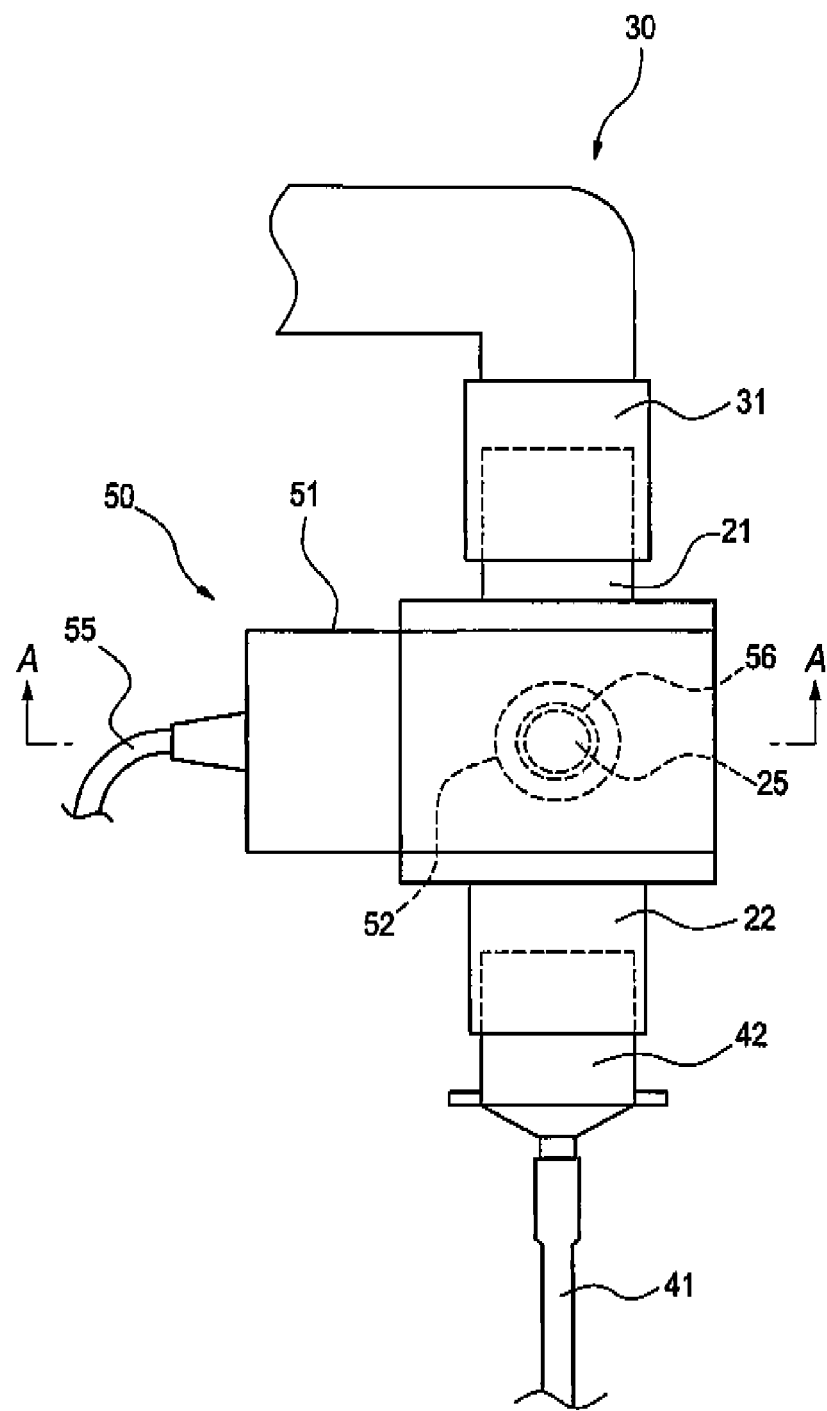
FIG. 2 is an enlarged side view enlargedly showing the vicinity of a respiratory airway adaptor of the respiratory waveform analyzer.
Figure 3:
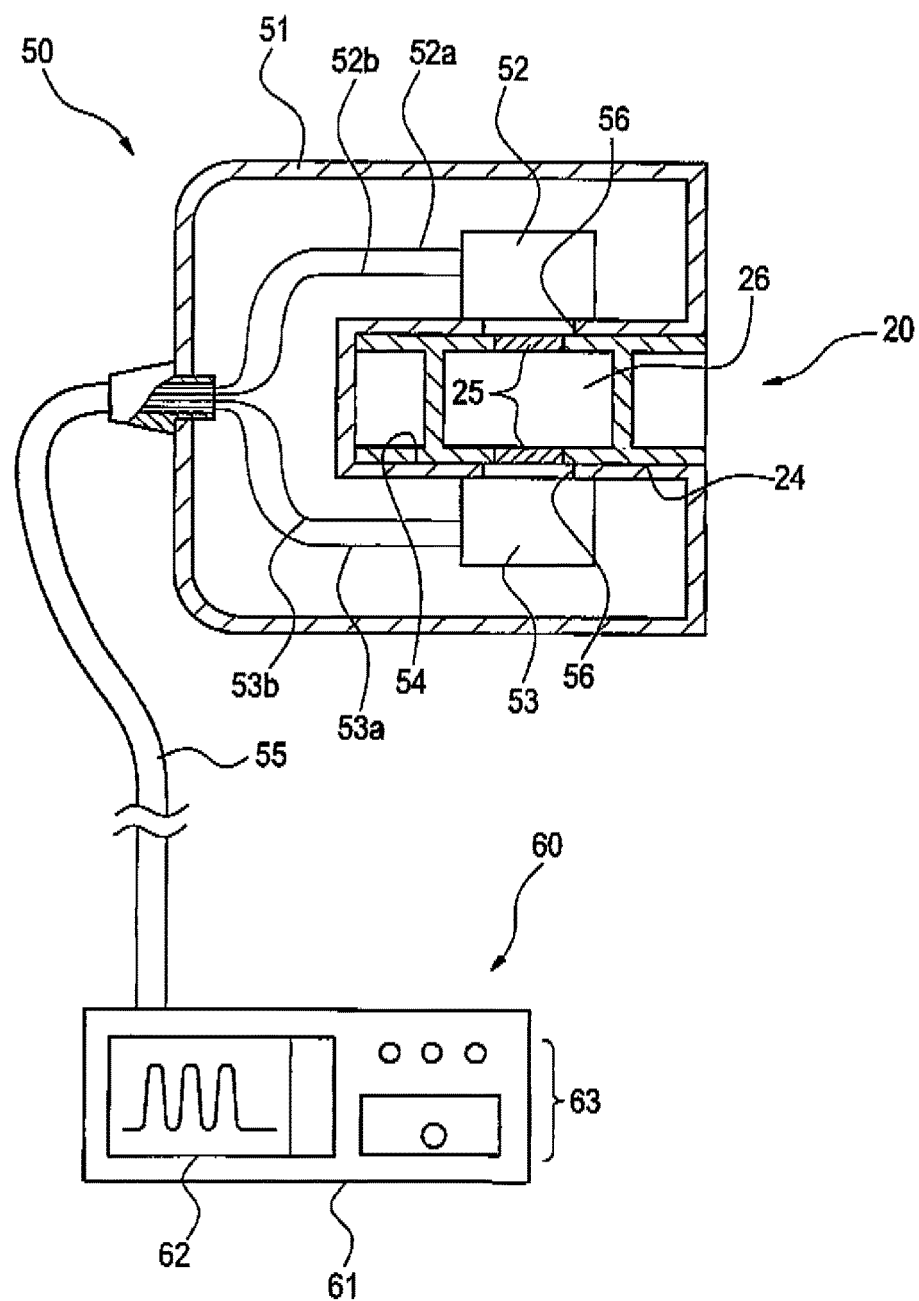
FIG. 3 is a sectional view of the A-A section of FIG. 2 as viewed in the direction of the arrows in FIG. 2.

FIG. 1 is an exploded perspective view showing the configuration of a respiratory waveform analyzer 10 of the embodiment, FIG. 2 is an enlarged side view enlargedly showing the vicinity of a respiratory airway adaptor 20 of the respiratory waveform analyzer 10, and FIG. 3 is a sectional view of the A-A section of FIG. 2 as viewed in the direction of the arrows in FIG. 2.

The respiratory waveform analyzer 10 is an apparatus which measures a temporal change of the $CO_2$ concentration in the expiration of a subject such as a patient who must undergo respiratory management, thereby monitoring the respiratory condition of the subject. The analyzer includes the respiratory airway adaptor 20, a Y-shaped adaptor 30, an insertion portion 40, a sensor portion 50, and a measuring device 60.

A respiratory airway 26 through which the respiratory gas of the subject is to pass is disposed in the respiratory airway adaptor 20. A connection port 21 which is connected to a connection port 31 of the Y-shaped adaptor 30, and a connection port 22 which is connected to a connection adaptor 42 of the insertion portion 40 are disposed on the both ends of the respiratory airway 26, respectively.

A set of sensor attaching faces 24 which are parallel to each other are formed at intermediate positions of the respiratory airway 26 in the respiratory airway adaptor 20, respectively. When the sensor portion 50 is attached to the respiratory airway adaptor 20, the sensor attaching faces 24 are in contact with the inner face of a recess 54 of the sensor portion 50. A transmissive window 25 which is configured by fitting a transmissive member into a circular vacant hole is disposed in each of the sensor attaching faces 24. The transmissive windows 25 are disposed at positions which correspond to openings 56 in the inner face of the recess 54 when the sensor portion 50 is attached, respectively.

The Y-shaped adaptor 30 has: the connection port 31 which is connected to the connection port 21 of the respiratory airway adaptor 20; an inspiratory air pipe 32 which is to be connected to an air supply source side of a ventilator; and an expiration air pipe 33 which is to be connected to an expiratory discharge valve side of the ventilator. The Y-shaped adaptor 30 is a member through which air that is supplied from, for example, the ventilator to the subject passes, and the expiration from the subject passes to the expiratory discharge valve side of the ventilator.

The insertion portion 40 has a tube 41 which is to be inserted into the airway of the subject, and a connection adaptor 42 which mediates connection between one end of the tube 41 and the connection port 22 of the respiratory airway adaptor 20.

The sensor portion 50 has: a sensor housing portion 51 which has a substantially U-like shape, and in which a light emitter 52 that emits infrared light, and a light receiver 53 that receives the infrared light from the light emitter 52, and that outputs a voltage the level of which corresponds to the intensity of the received light are disposed; and a connection cable 55 through which the sensor housing portion 51 is connected to the body unit 61 of the measuring device 60. As shown in FIGS. 1 and 3, the light emitter 52 and the light receiver 53 are opposed to each other across the recess 54 formed in the sensor housing portion 51.

As shown in FIGS. 2 and 3, the circular openings 56 are disposed at the positions where the light emitter 52 and the light receiver 53 are disposed, in the inner face of the recess 54. As shown in FIG. 3, the light emitter 52 is electrically connected through wirings 52a, 52b, and the light receiver 53 is electrically connected through wirings 53a, 53b to the body unit 61 of the measuring device 60.

In the embodiment, the light emitter 52 emits infrared light in accordance with the electric power supplied from the body unit 61. As the light emitter 52, a device for emitting light of a wavelength at which the rate of absorption by $CO_2$ gas is higher as compared with the longer and shorter wavelength sides is used. When receiving the light from the light emitter 52, therefore, the light receiver 53 outputs a voltage the level of which is substantially proportional to the $CO_2$ concentration. The light emitter 52 is a single light source emitting light having a large band and the light receiver 53 narrows the band by using a filter when receiving the light.

The measuring device 60 has the body unit 61 which is connected to the sensor housing portion 51 of the sensor portion 50 through a connection cable 55, and a displaying portion 62 and operating portion 63 which are disposed in the front face of the body unit 61.

In a state where the respiratory airway adaptor 20, the Y-shaped adaptor 30, and the insertion portion 40 are assembled together, and the sensor portion 50 is attached to the respiratory airway adaptor 20, the respiratory waveform analyzer 10 is used for measuring the concentration of carbon dioxide ($CO_2$ concentration) in the expiration or inspiration (hereinafter, both are generally referred as "respiration") of the subject.

In the measurement by the respiratory waveform analyzer 10, the respiration of the subject which passes through the respiratory airway 26 of the respiratory airway adaptor 20 is irradiated with the infrared light which is emitted from the light emitter 52 in accordance with the electric power supplied from the measuring device 60, and transmitted light is received by the light receiver 53. Then, the light receiver 53 outputs a voltage the level of which corresponds to the intensity of the received light, to the measuring device 60.

Based on the voltage from the light receiver 53, the measuring device 60 detects the partial pressure of carbon dioxide in the pressure of the respiration which passes through the respiratory airway 26. The partial pressure of carbon dioxide has a value corresponding to the concentration of $CO_2$ contained in the respiration which passes through the respiratory airway 26. In the following description, therefore, the partial pressure of carbon dioxide detected by the measuring device 60 is referred to as the $CO_2$ concentration.

The measuring device 60 generates a waveform based on a temporal change of the detected $CO_2$ concentration, and displays the waveform on the displaying portion 62. In the following description, the waveform is referred to as the respiratory waveform. Various measurement conditions in the measurement, a change of the manner of displaying the respiratory waveform on the displaying portion 62, and the like can be set as predetermined ones by operating the operating portion 63 of the measuring device 60.

Hereinafter, the detection of the $CO_2$ concentration by the measuring device 60, and generation and analysis of the respiratory waveform will be described in more detail.

Figure 4:
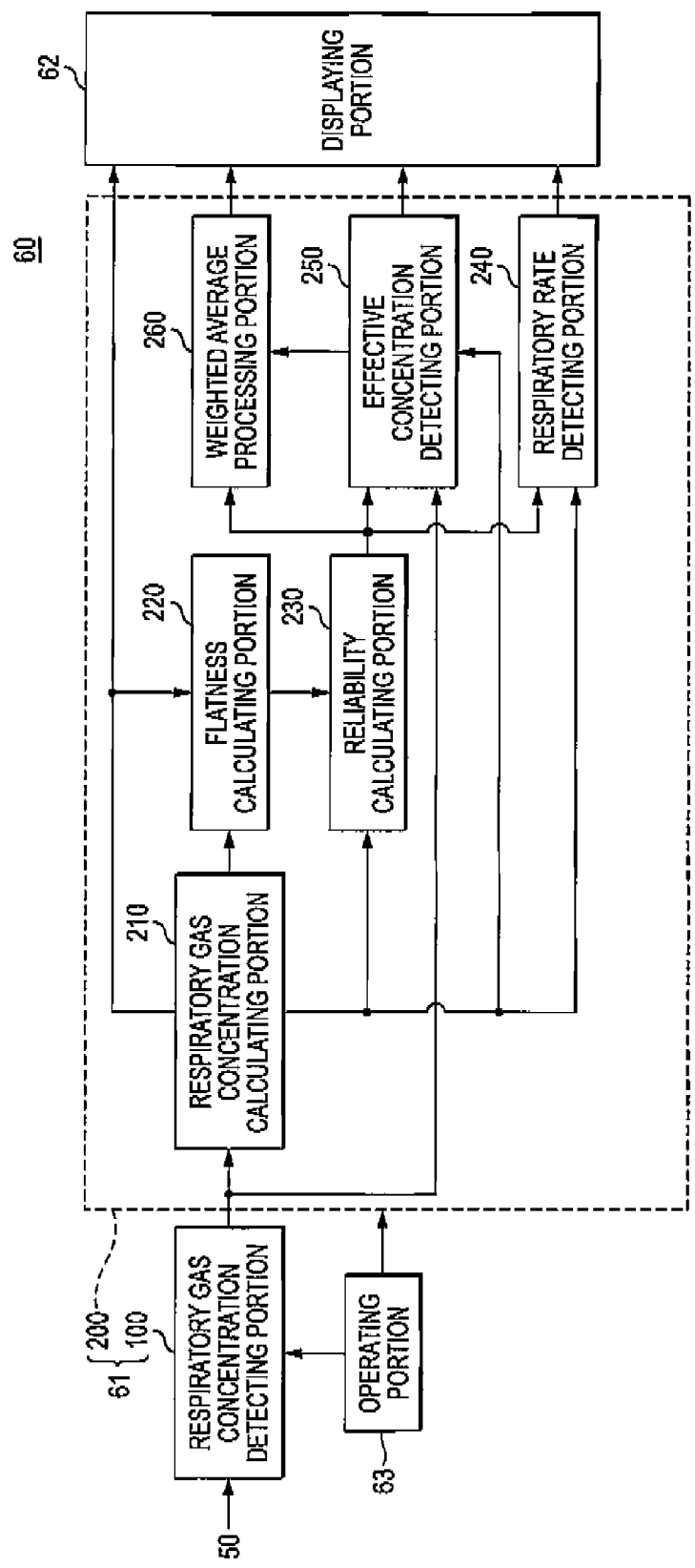
FIG. 4 is a functional block diagram showing the configuration of a measuring device.

FIG. 4 is a functional block diagram showing the configuration of the measuring device 60. The illustration of the configuration related to the power supply to the light emitter 52 is omitted (the same shall apply to the other functional block diagrams). As shown in FIG. 4, the measuring device 60 has a respiratory gas concentration detecting portion 100 and a calculating processing portion 200, in the body unit 61. The calculating processing portion 200 includes a respiratory gas concentration calculating portion 210, a flatness calculating portion 220, a reliability calculating portion 230, a respiratory rate detecting portion 240, an effective concentration detecting portion 250, and a weighted average processing portion 260.

When receiving an analog output signal which is supplied in, for example, a time continuous manner from the sensor portion 50, the respiratory gas concentration detecting portion 100 converts the analog signal to a digital respiratory gas signal which corresponds to the level of the analog signal, and supplies the digital signal to the respiratory gas concentration calculating portion 210 and the effective concentration detecting portion 250. The respiratory gas concentration detecting portion 100 is configured by an A/D converter and the like. The respiratory gas concentration detecting portion 100 and the respiratory gas concentration calculating portion 210 correspond to the respiratory gas concentration generating portion in the invention.

The respiratory gas concentration calculating portion 210 receives the voltage (respiratory gas signal) of a level which corresponds to the $CO_2$ concentration supplied from the respiratory gas concentration detecting portion 100, and generates the respiratory waveform. The respiratory gas concentration calculating portion 210 supplies the generated respiratory waveform to the displaying portion 62, the flatness calculating portion 220, the reliability calculating portion 230, the respiratory rate detecting portion 240, and the effective concentration detecting portion 250.

The flatness calculating portion 220 calculates the flatness indicative of the flat degree of the respiratory waveform supplied from the respiratory gas concentration calculating portion 210. The flatness calculating portion 220 calculates the difference between previous and current $CO_2$ concentrations at specific time intervals, and then calculates the flatness based on degree of the difference. The degree of the difference may be an absolute value of the difference and may be obtained by raising the difference to the power of the even number. Specifically, the flatness calculating portion 220 calculates the flatness by using the following calculation expression (Exp. 1). The flatness calculating portion 220 sequentially outputs the calculated flatness in a time series manner to the reliability calculating portion 230.

$$Y[0]=1/\{\Sigma(D\Delta tCO2)^2+1\} \quad [\text{Exp. 1}]$$

Y[0]: current flatness in the respiratory waveform
$D\Delta tCO2$: difference between previous and current $CO_2$ concentrations at time interval $\Delta t$ In Exp. 1 above, the time interval $\Delta t$ may be, for example, 0.05 seconds, and $\Sigma(D\Delta tCO2)^2$ may be, for example, an accumulated value of the squares of the differences which are calculated during 0.1 seconds immediately before the calculation of the flatness. As indicated by Exp. 1 above, the flatness calculated by the flatness calculating portion 220 is a function of the accumulated value of the squares of the differences, and has the maximum value when the accumulated value is minimum.

Figure 5:
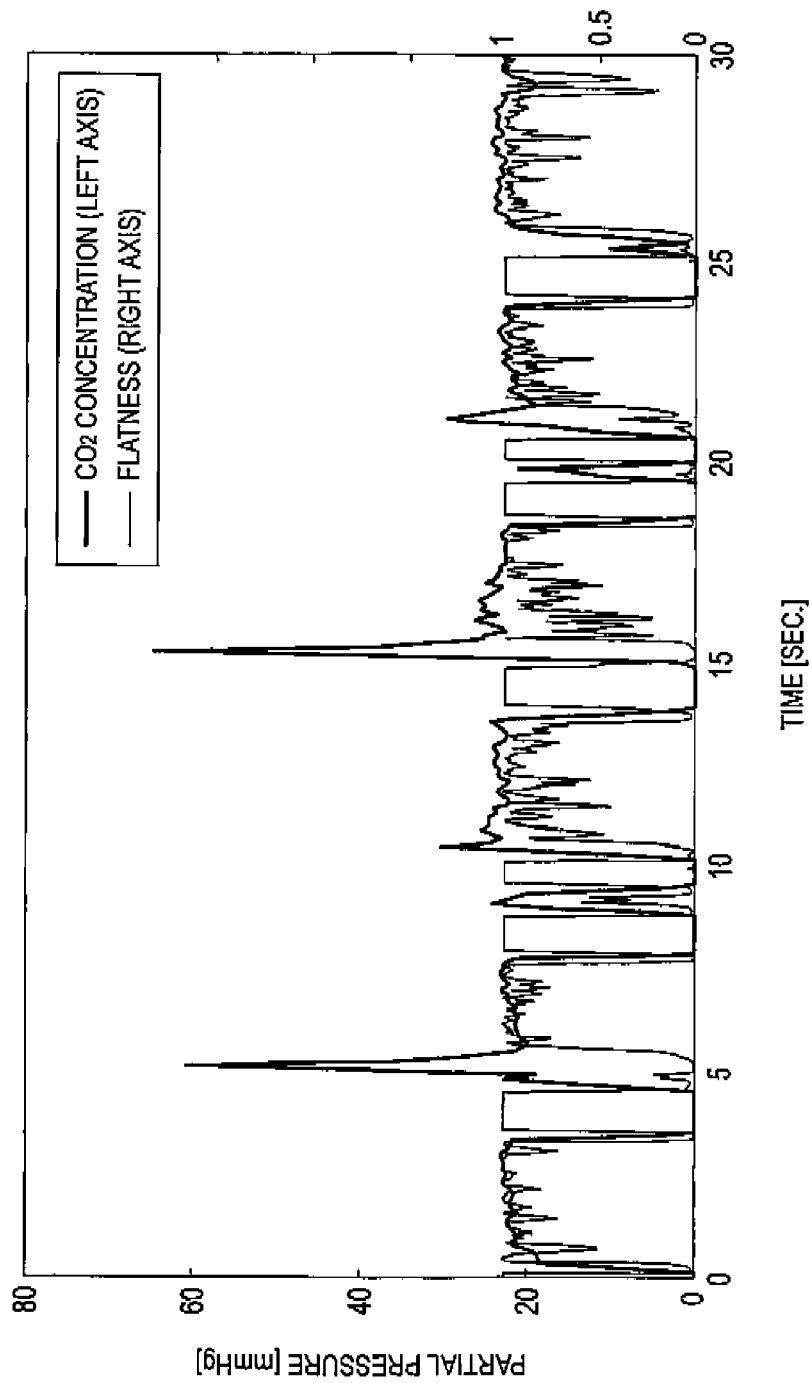
FIG. 5 is a view showing an example of a respiratory waveform and the flatness of the respiratory waveform.

FIG. 5 shows an example of the respiratory waveform and the flatness of the respiratory waveform. In the respiratory waveform shown in FIG. 5, the flatness is reduced in portions (the vicinities of 5 and 15 seconds in FIG. 5) where the temporal change of the $CO_2$ concentration is violent due to, for example, adhesion of water droplets to the transmissive windows 25 of the respiratory airway adaptor 20, and those (the vicinities of 9 and 20 seconds in FIG. 5) where the $CO_2$ concentration is varied due to spontaneous respiration of the subject or the like.

The reliability calculating portion 230 calculates the reliability of the respiratory waveform on the basis of the degree of the flatness supplied from the flatness calculating portion 220, and the respiratory waveform supplied from the respiratory gas concentration calculating portion 210. Specifically, the reliability calculating portion 230 calculates, as the reliability, a value in which the flatness calculated by the flatness calculating portion 220 is multiplied with the value (the degree of the $CO_2$ concentration) of the respiratory waveform corresponding to the timing of calculating the flatness. Then, the reliability calculating portion 230 sequentially outputs the calculated reliability in a time series manner to the respiratory rate detecting portion 240, the effective concentration detecting portion 250, and the weighted average processing portion 260.

Figure 6:
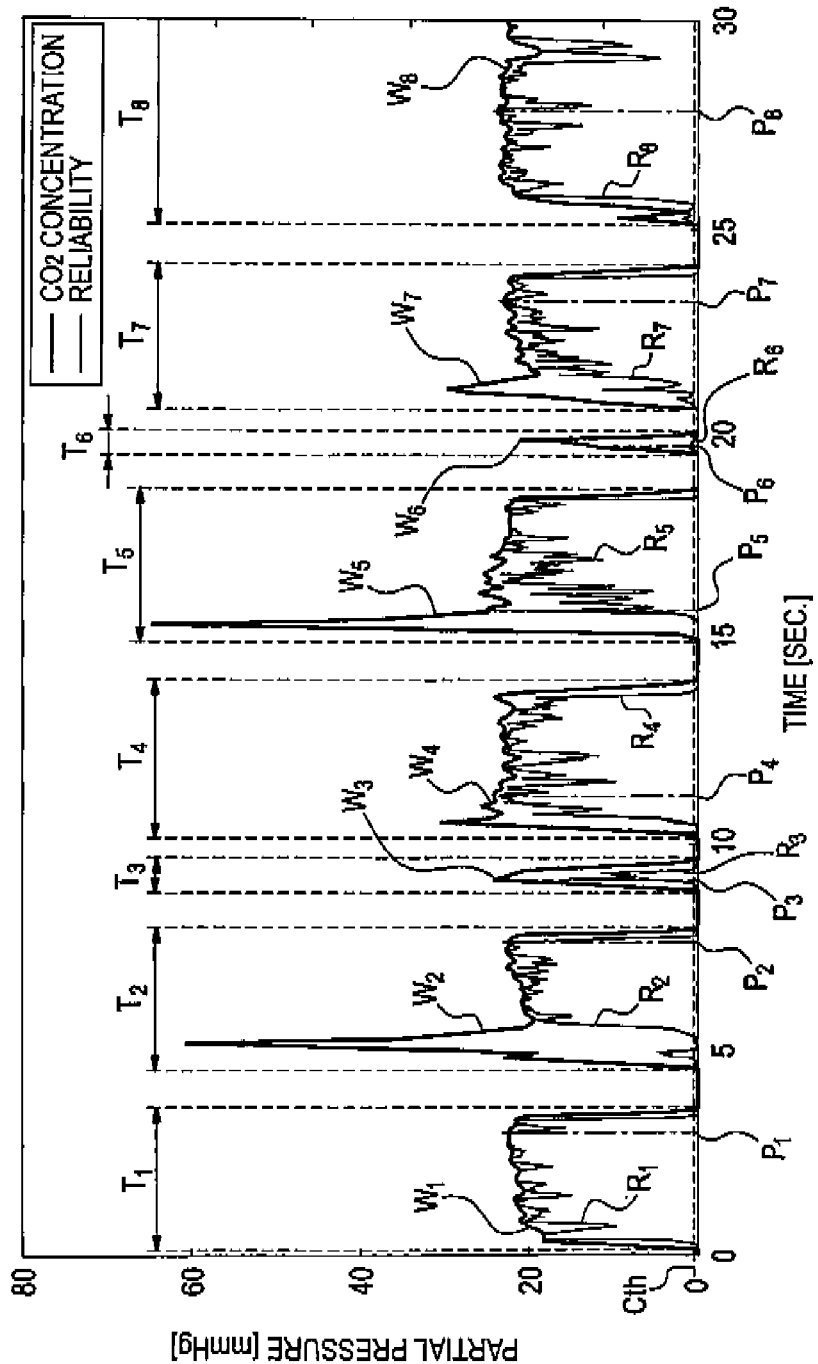
FIG. 6 is a view showing an example of a respiratory waveform and the reliability of the respiratory waveform.

FIG. 6 shows an example of the respiratory waveform and the reliability of the respiratory waveform. As shown in FIG. 6, at a timing when the flatness corresponding to the respiratory waveform is reduced, the reliability of the respiratory waveform shows a tendency to reduce irrespective of the degree of the $CO_2$ concentration. Namely, the reliability shows a reduction tendency when the respiratory waveform is largely varied in a short time period because, for example, water droplets adhere to the transmissive windows 25 of the respiratory airway adaptor 20, or the subject performs spontaneous respiration.

The effective concentration detecting portion 250 detects the time period corresponding to one cycle from the respiratory waveform supplied from the respiratory gas concentration calculating portion 210. In the embodiment, the effective concentration detecting portion 250 detects a portion of the respiratory waveform, extending from a timing when the $CO_2$ concentration exceeds a predetermined threshold ($C_{th}$) to that when the $CO_2$ concentration again falls below the threshold, as an expiratory waveform in one cycle of the respiratory waveform. In the respiratory waveform shown in FIG. 6, for example, the effective concentration detecting portion 250 detects eight expiratory waveforms ($W_1$ to $W_8$).

The effective concentration detecting portion 250 detects time periods respectively corresponding to the expiratory waveforms, as concentration detecting time periods ($T_1$ to $T_8$) in the expiratory waveforms. As shown in FIG. 6, for example, the effective concentration detecting portion 250 detects the concentration detecting concentration detecting time periods ($T_1$ to $T_8$) for the eight expiratory waveforms ($W_1$ to $W_8$), respectively.

The effective concentration detecting portion 250 extracts reliabilities in the respective concentration detecting time periods, and detects timings when the value of the reliability is maximum. As shown in FIG. 6, for example, the effective concentration detecting portion 250 extracts the reliabilities ($R_1$ to $R_8$) in the respective concentration detecting time periods ($T_1$ to $T_8$), and detects the timings ($P_1$ to $P_8$) when the value of the reliability is maximum in each of the concentration detecting time periods.

The effective concentration detecting portion 250 detects the value ($CO_2$ concentration) of the expiratory waveform at the timing when the reliability is maximum in each of the concentration detecting time periods, as the effective concentration in the expiratory waveform. As shown in FIG. 6, for example, the effective concentration detecting portion 250 detects the $CO_2$ concentrations at the timings ($P_1$ to $P_8$) which are detected in the respective concentration detecting time periods ($T_1$ to $T_8$), as the effective concentrations in the corresponding expiratory waveforms ($W_1$ to $W_8$), respectively.

At a timing when the respiratory waveform is largely varied, the reliability is reduced as described above, and hence the effective concentration detecting portion 250 does not detect the $CO_2$ concentration at the timing as the effective concentration.

As described above, the respiratory waveform analyzer 10 of the embodiment can correctly know noise components in the respiratory waveform on the basis of the reliability calculated by the reliability calculating portion 230. Even in the case where the respiratory waveform is largely varied due to, for example, adhesion of water droplets to the transmissive windows 25 of the respiratory airway adaptor 20, when the reliability is used, a peak of the varying portion is not detected as the effective concentration, and the effective $CO_2$ concentration in each cycle of the respiratory waveform can be detected with a higher accuracy.

Figure 7:
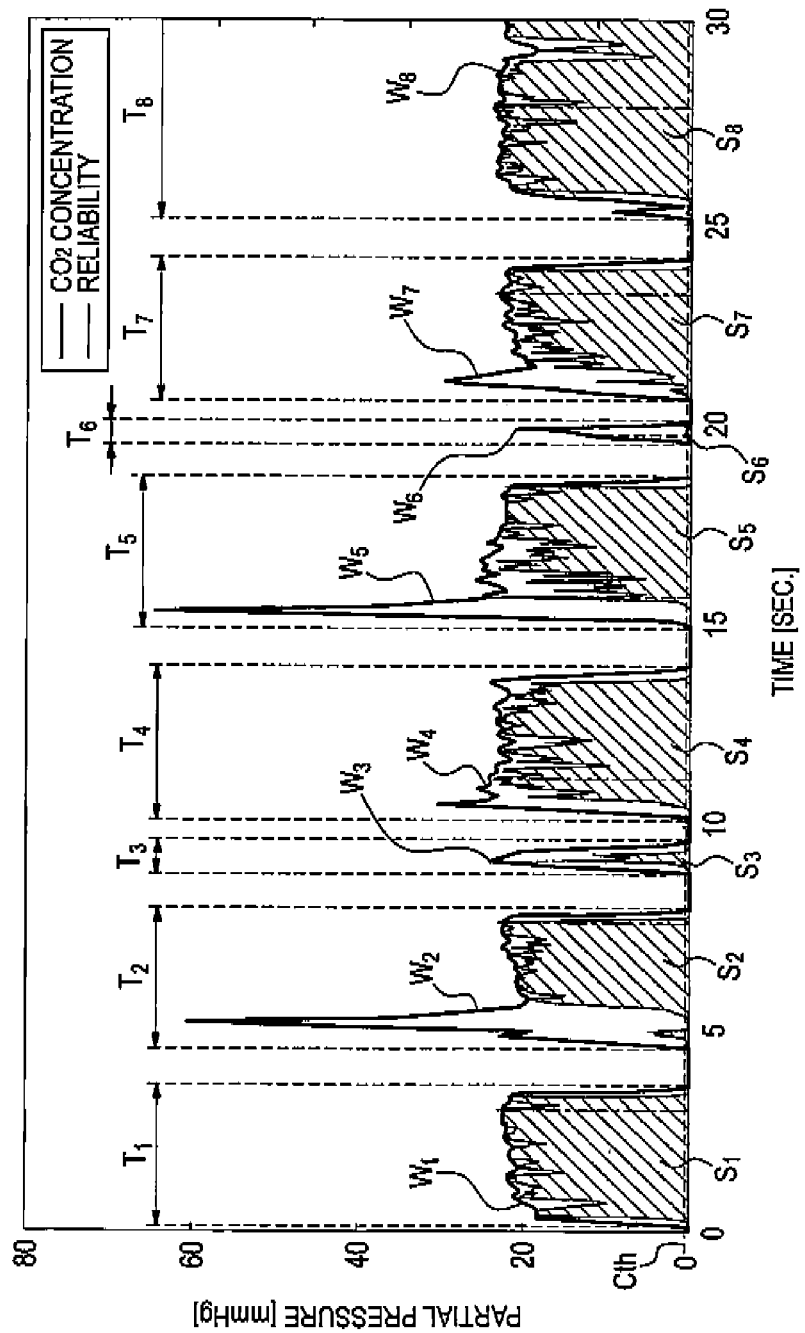
FIG. 7 is a view showing a respiratory waveform, the reliability of the respiratory waveform, and an accumulated value of reliabilities during each of concentration detecting time periods.

FIG. 7 shows a respiratory waveform, the reliability of the respiratory waveform, and the accumulated value of reliabilities during each of concentration detecting time periods. The respiratory waveform and reliability of the respiratory waveform which are shown in FIG. 7 are identical with those shown in FIG. 6. Therefore, the expiratory waveforms ($W_1$ to $W_8$), concentration detecting time periods ($T_1$ to $T_8$), and the like which are denoted by the same reference numerals as those of FIG. 6 are identical with those shown in FIG. 6, and hence their description is omitted.

In the embodiment, the effective concentration detecting portion 250 accumulates the reliabilities in the respective concentration detecting time periods, and compares the value of the accumulation with a predetermined lower-limit reliability. Then, the effective concentration detecting portion 250 detects the effective concentration, only in concentration detecting time periods when the accumulated value exceeds the lower-limit reliability.

The detection will be described more specifically with reference to the respiratory waveform shown in FIG. 7. The effective concentration detecting portion 250 accumulates the reliabilities in each of the concentration detecting time periods ($T_1$ to $T_8$), to calculate accumulated values ($S_1$ to $S_8$) respectively corresponding to the concentration detecting time periods. In the effective concentration detecting portion 250, for example, a value which is larger than the accumulated values ($S_3$, $S_6$) of the reliabilities corresponding to the expiratory waveforms ($W_3$, $W_6$) generated by spontaneous respiration of the subject, and which is smaller than any of the accumulated values ($S_1$, $S_2$, $S_4$, $S_5$, $S_7$, $S_8$) of the reliabilities corresponding to the normal expiratory waveforms ($W_1$, $W_2$, $W_4$, $W_5$, $W_7$, $W_8$) with respect to the air supply from the ventilator is stored as the lower-limit reliability.

Then, the effective concentration detecting portion 250 calculates the accumulated values ($S_1$ to $S_8$) of the reliabilities in the respective concentration detecting time periods ($T_1$ to $T_8$), and compares the accumulated values with the lower-limit reliability. The effective concentration detecting portion 250 detects the effective concentration in only the concentration detecting time periods ($T_1$, $T_2$, $T_4$, $T_5$, $T_7$, $T_8$) corresponding to, among the accumulated values, the accumulated values ($S_1$, $S_2$, $S_4$, $S_5$, $S_7$, $S_8$) which are larger than the lower-limit reliability. The effective concentration detecting portion 250 supplies the detected effective concentrations (hereinafter, indicated by $C_1$, $C_2$, $C_4$, $C_5$, $C_7$, $C_8$) to the weighted average processing portion 260 and the displaying portion 62. The displaying portion 62 displays the effective concentrations.

In the respiratory waveform analyzer 10 of the embodiment, as described above, the effective concentration detecting portion 250 does not detect the effective concentration with respect to an expiratory waveform which is generated by, for example, spontaneous respiration of the subject, and which has a low reliability, and therefore can detect the effective $CO_2$ concentration with respect to only normal expiration from the subject for the air supply from the ventilator.

The respiratory rate detecting portion 240 detects the respiratory rate per unit time period, on the basis of the respiratory waveform supplied from the respiratory gas concentration calculating portion 210 and the reliability supplied from the reliability calculating portion 230. Similarly with the effective concentration detecting portion 250, specifically, the respiratory rate detecting portion 240 detects, for example, a portion of the respiratory waveform, extending from a timing when the $CO_2$ concentration exceeds a predetermined threshold to that when the $CO_2$ concentration again falls below the threshold, as an expiratory waveform in one cycle of the respiratory waveform.

Then, the respiratory rate detecting portion 240 calculates the accumulated values of the reliabilities supplied from the reliability calculating portion 230, and, similarly with the effective concentration detecting portion 250, compares the accumulated values with the lower-limit reliability. With respect to only expiratory waveforms corresponding to, among the accumulated values, accumulated values which exceed the lower-limit reliability, then, the respiratory rate detecting portion 240 detects the respiratory rate of the subject per unit time period, and supplies numerical data of the respiratory rate to the displaying portion 62. The displaying portion 62 displays the respiratory rate of the subject per unit time period.

In the embodiment, as described above, the respiratory rate is not counted with respect to an expiratory waveform which is generated by, for example, spontaneous respiration of the subject, and which has a low reliability. Therefore, the respiratory rate based on the respiratory motion of the subject with respect to the air supply from the ventilator can be detected more correctly.

In the case where the plurality of effective concentrations are detected from the respiratory waveform in the effective concentration detecting portion 250, the weighted average processing portion 260 calculates a weighted average value in which the effective concentrations are weighted respectively in accordance with the degrees of accumulated values of the reliabilities corresponding to the effective concentrations, and then averaged.

In the respiratory waveform shown in FIG. 7, for example, the weighted average processing portion 260 calculates a weighted average value on the basis of the following calculation expression (Exp. 2), from the effective concentrations ($C_1$, $C_2$, $C_4$, $C_5$, $C_7$, $C_8$) which are detected from the expiratory waveforms $W_1$, $W_2$, $W_4$, $W_5$, $W_7$, $W_8$ by the effective concentration detecting portion 250, and the accumulated values ($S_1$, $S_2$, $S_4$, $S_5$, $S_7$, $S_8$) of the reliabilities respectively corresponding to the correct expiratory waveforms. Then, the weighted average processing portion 260 supplies the calculated weighted average value to the displaying portion 62. The displaying portion 62 displays the weighted average value.

$$AV=(C1 \times S1+C2 \times S2+C4 \times S4+C5 \times S5+C7 \times S7+C8 \times S8)/(S1+S2+S4+S5+S7+S8) \quad [\text{Exp. 2}]$$

AV: weighted average value

Furthermore, the weighted average processing portion 260 may update the weighted average value in accordance with that the effective concentration detecting portion 250 newly detects the effective concentration on the basis of the respiratory waveform. For example, the weighted average processing portion 260 may update the weighted average value, at constant time intervals in accordance with the new effective concentration which is detected by the effective concentration detecting portion 250, and the degree of the accumulated value of reliabilities corresponding to the effective concentration.

In the respiratory waveform analyzer 10 of the embodiment, as described above, a weighted average value is calculated in which the effective concentrations detected from the respiratory waveform are weighted and averaged in accordance with accumulated values of the reliabilities of the respiratory waveform. Therefore, the detected effective concentrations are displayed as they are on the displaying portion 62, and also can be displayed as the average value in which the effective concentrations calculated from the expiratory waveform having low noise components are more reflected.

Figure 8:
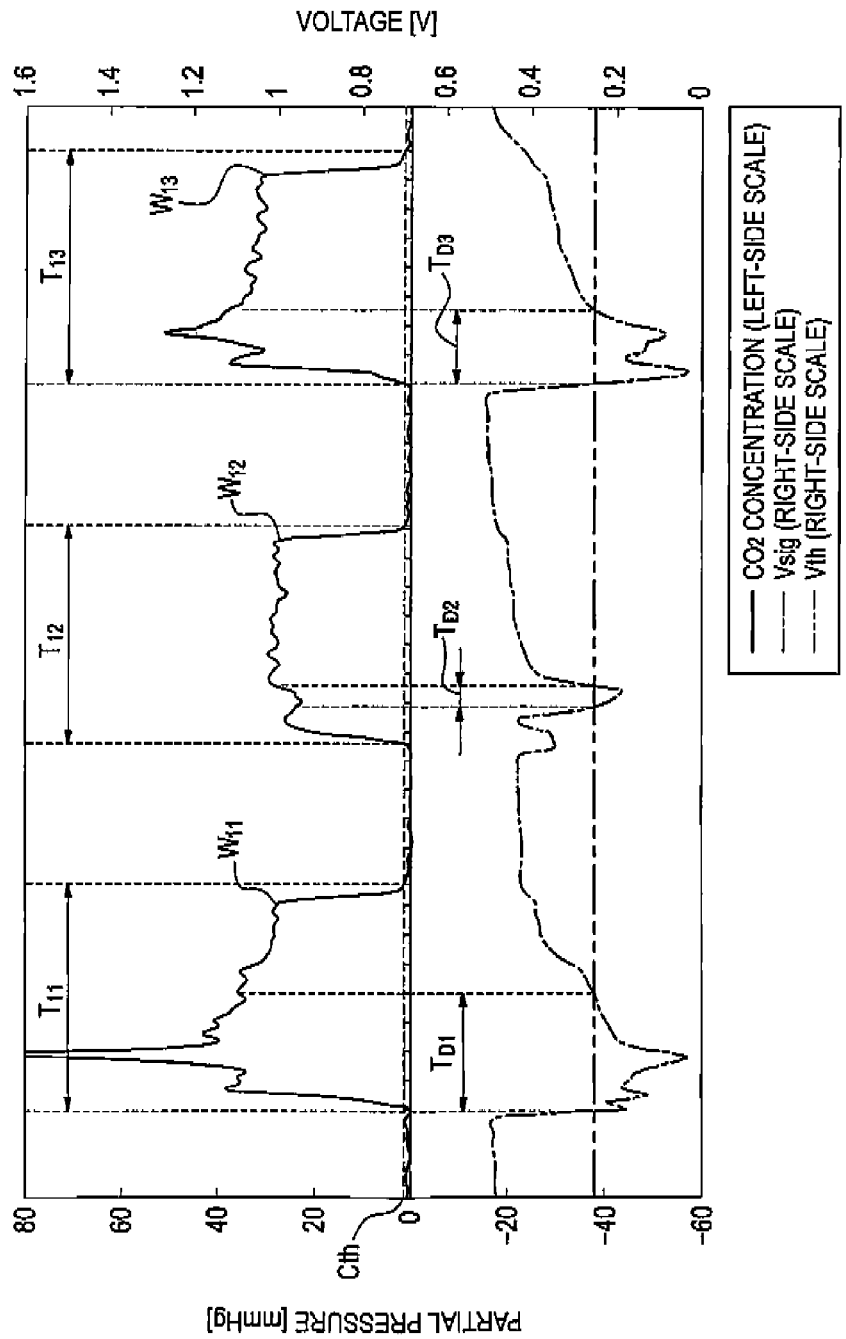
FIG. 8 is a view showing an example of a waveform of a voltage supplied from a respiratory gas concentration detecting portion, and a respiratory waveform which is generated on the basis of the waveform of the voltage.

FIG. 8 shows an example of a waveform of the voltage ($V_{sig}$) supplied from the respiratory gas concentration detecting portion 100, and a respiratory waveform which is generated on the basis of the waveform of the voltage. In the respiratory waveform shown in FIG. 8, similarly with that shown in FIG. 6, waveforms of $W_{11}$ to $W_{13}$ are respiratory waveforms which are detected by the effective concentration detecting portion 250 on the basis of comparison with the predetermined threshold ($C_{th}$). In the figure, $T_{11}$ to $T_{13}$ indicate concentration detecting time periods for the expiratory waveforms ($W_{11}$ to $W_{13}$), respectively.

In a use of the respiratory waveform analyzer 10, when the intensity of the received light in the light receiver 53 of the sensor portion 50 is lowered by, for example, adhesion of water droplets to the transmissive windows 25 of the respiratory airway adaptor 20, also the value of the voltage supplied from the light receiver 53 is lowered in accordance with the lowering of the intensity. At this time, the respiratory waveform which is generated by the respiratory gas concentration calculating portion 210 is sometimes abruptly varied irrespective of the actual degree of the concentration of $CO_2$ contained in the respiration which passes through the respiratory airway 26.

In the measuring device 60, by contrast, the effective concentration detecting portion 250 receives the voltage ($V_{sig}$) supplied from the respiratory gas concentration detecting portion 100, and compares the voltage with a preset lower-limit voltage. Then, the effective concentration detecting portion 250 removes time periods in which the value of the voltage ($V_{sig}$) is smaller than the lower-limit voltage ($V_{th}$), from the concentration detecting time periods for the respiratory waveform. In the respiratory waveform shown in FIG. 8, for example, the effective concentration detecting portion 250 detects the effective concentration in time periods that are obtained by removing time periods ($T_{D1}$ to $T_{D3}$) in which the value of the voltage ($V_{sig}$) is smaller than the lower-limit voltage ($V_{th}$) from the concentration detecting time periods ($T_{11}$ to $T_{13}$) for the expiratory waveforms ($W_{11}$ to $W_{13}$).

In the respiratory waveform analyzer 10 of the embodiment, as described above, the effective concentration is detected after noise components in the respiratory waveform are removed, and hence the effective concentration of $CO_2$ contained in the respiration of the subject can be detected more correctly.

Figure 9:
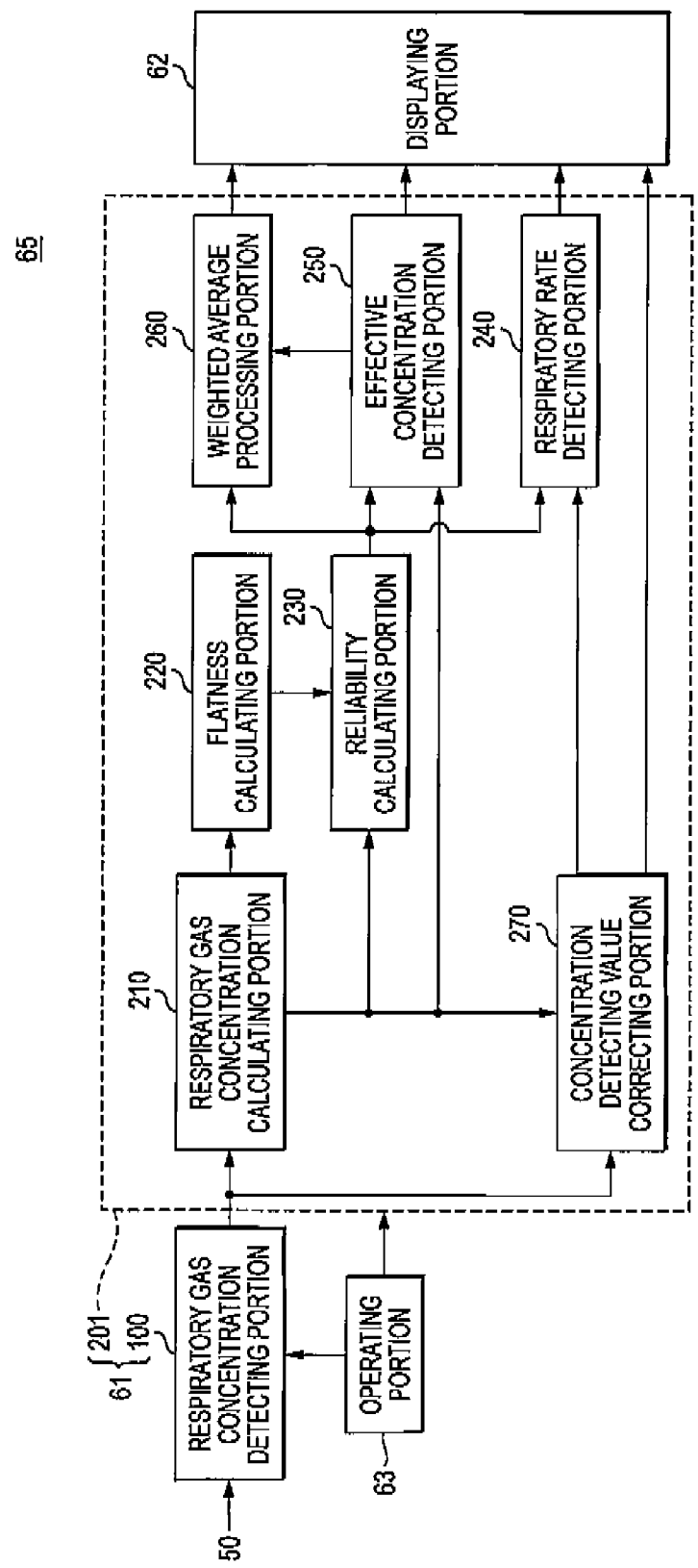
FIG. 9 is a functional block diagram showing the configuration of a measuring device in another example of the embodiment.

FIG. 9 is a functional block diagram showing the configuration of a measuring device 65 in another example of the embodiment. In the measuring device 65, components similar to those of the measuring device 60 which has been described with reference to FIG. 4 are denoted by the same reference numerals, and their description is omitted.

The measuring device 65 has the respiratory gas concentration detecting portion 100 and a calculating processing portion 201, in the body unit 61. The calculating processing portion 201 includes a concentration detection value correcting portion 270 in addition to the components which are included by the calculating processing portion 200.

The concentration detection value correcting portion 270 receives the voltage supplied from the respiratory gas concentration detecting portion 100, and corrects the respiratory waveform in accordance with the ratio of the voltage value to a predetermined reference voltage value. Specifically, the concentration detection value correcting portion 270 calculates a correction value in which the $CO_2$ concentration corresponding to the voltage value in the respiratory waveform is corrected on the basis of, for example, the following calculation expression (Exp. 3), and outputs a time series of the correction value as a corrected respiratory waveform to the displaying portion 62 and the respiratory rate detecting portion 240. The displaying portion 62 displays the corrected respiratory waveform.

$$F\_CO2[0]=a(Vsig/Vsig0)^b \times Cp+[1-a(Vsig/Vsig0)^b] \times F\_CO2[1] \quad [\text{Exp. 3}]$$

F_CO2[0]: correction value of the $CO_2$ concentration
F_CO2[1]: $CO_2$ concentration at the previous timing
Cp: current $CO_2$ concentration
Vsig: current voltage value
Vsig0: reference voltage value
a: weighting adjustment factor
b: weighting adjustment factor In Exp. 3 above, the reference voltage value (Vsig0) is a voltage value which is supplied from the respiratory gas concentration detecting portion 100 when the measurement is performed by the respiratory waveform analyzer 10 in a state where no gas exists in the respiratory airway 26 of the respiratory airway adaptor 20.

The weighting adjustment factors (a, b) are factors for adjusting the correction value to a value in which the ratio (Vsig/Vsig0) of a change of the current voltage value (the voltage value to be corrected) to the reference voltage value is more reflected to the current $CO_2$ concentration (Cp), or that in which the ratio is more reflected to the $CO_2$ concentration (F_CO2[1]) at the previous timing. In the embodiment, preferably, a is a value in the range of 0 to 1, and b is a value which is equal to or larger than 0.

Figure 10:
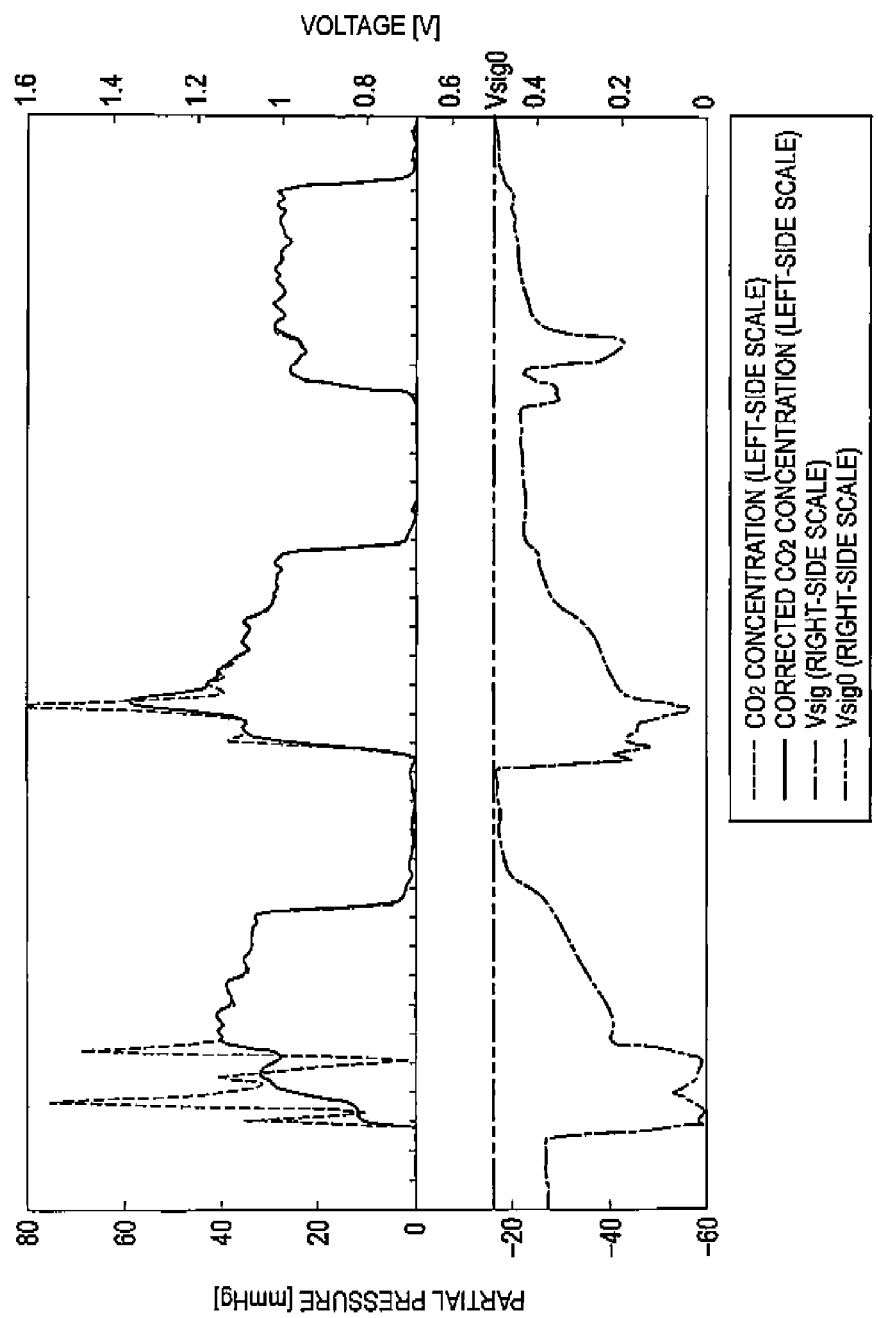
FIG. 10 is a view showing an example of the waveform of the voltage supplied from the respiratory gas concentration detecting portion, the respiratory waveform which is generated on the basis of the waveform of the voltage, and a corrected respiratory waveform, in the measuring device.

FIG. 10 shows an example of the waveform of the voltage ($V_{sig}$) supplied from the respiratory gas concentration detecting portion 100, the respiratory waveform which is generated on the basis of the waveform of the voltage, and a corrected respiratory waveform, in the measuring device 65. The waveform indicated by "$CO_2$ CONCENTRATION" in FIG. 10 is the respiratory waveform which is generated by the respiratory gas concentration calculating portion 210 on the basis of the voltage ($V_{sig}$) supplied from the respiratory gas concentration detecting portion 100, and the waveform indicated by "CORRECTED $CO_2$ CONCENTRATION" in FIG. 10 is the respiratory waveform which is obtained by correcting the waveform indicated by "$CO_2$ CONCENTRATION", in accordance with the calculation expression of Exp. 3 above by the concentration detection value correcting portion 270.

In the example, both the weighting adjustment factors (a, b) in Exp. 3 above are set to 1. In the example, therefore, the concentration detection value correcting portion 270 calculates the correction value (F_CO2[0]) in which, as the ratio of the voltage ($V_{sig}$) supplied from the respiratory gas concentration detecting portion 100 to the reference voltage value ($V_{sig0}$) is smaller, the $CO_2$ concentration (Cp) generated by the respiratory gas concentration calculating portion 210 on the basis of the voltage ($V_{sig}$) is made smaller in accordance with the ratio.

Even when the voltage ($V_{sig}$) is made to a small value in which the $CO_2$ concentration of the respiration that passes through the respiratory airway 26 is not reflected, by the lowering of the intensity of the received light in the light receiver 53 due to a measurement error cause such as adhesion of water droplets to the transmissive windows 25 of the respiratory airway adaptor 20, therefore, the concentration detection value correcting portion 270 can generate a respiratory waveform in which an abrupt change of the $CO_2$ concentration (Cp) due to the measurement error cause is mitigated.

Furthermore, the respiratory rate detecting portion 240 can detect more correctly the respiratory rate of the subject per unit time period, and the displaying portion 62 can display a respiratory waveform which is less affected by the measurement error cause, and which is more similar to the $CO_2$ concentration of the respiration of the subject.

Water which is generated in the respiratory circuit during the use of the respiratory waveform analyzer 10 of the embodiment constitutes not only the error cause of the measurement of the $CO_2$ concentration as described above, but also may constitute a cause of pneumonia when the patient erroneously sucks the water. Therefore, the generation of water must be detected more correctly. Hereinafter, the respiratory waveform analyzer 10 which can solve such a problem will be exemplarily described.

Figure 11:
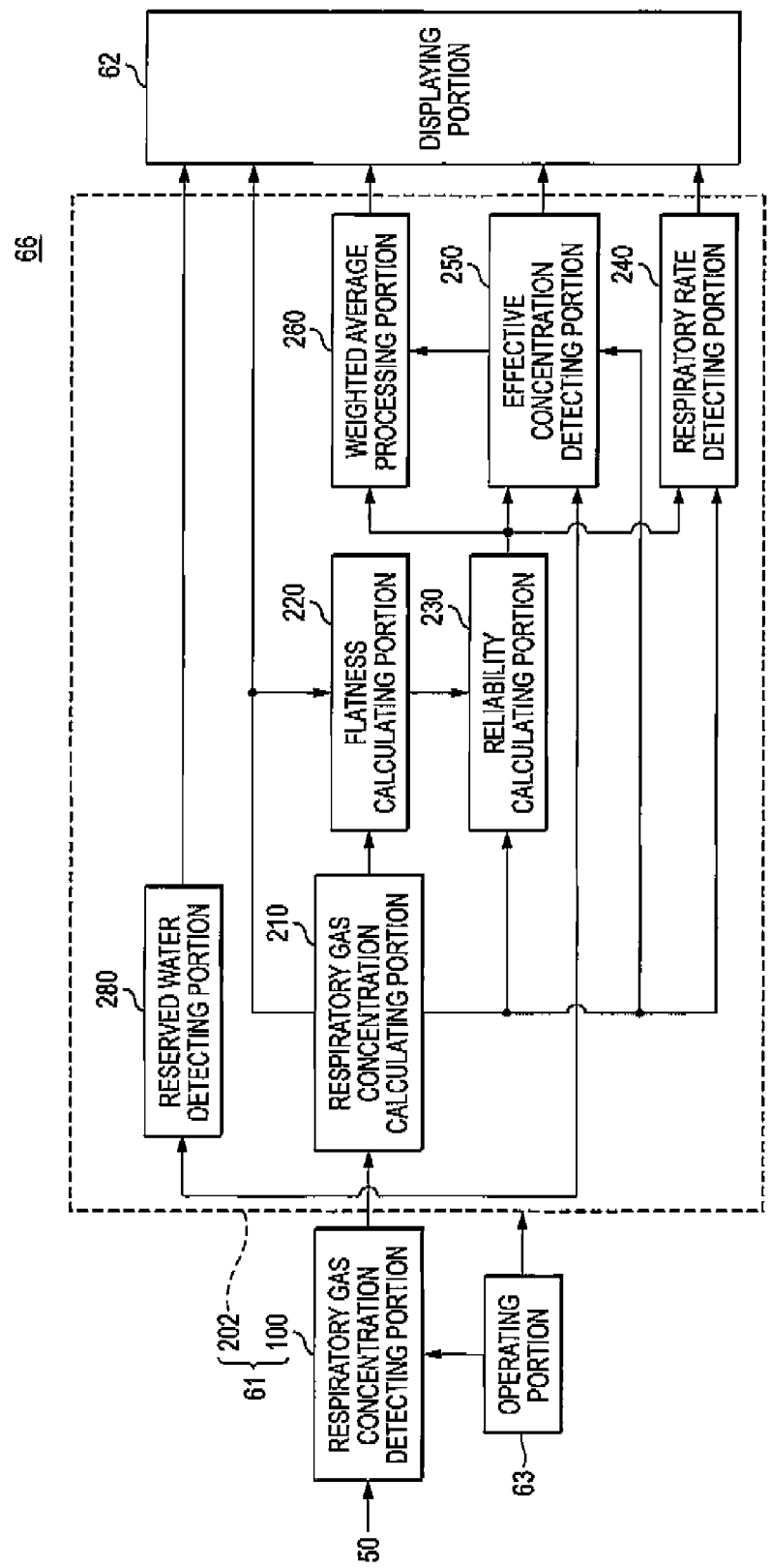
FIG. 11 is a functional block diagram showing the configuration of a measuring device in a further example of the embodiment.

FIG. 11 is a functional block diagram showing the configuration of a measuring device 66 in a further example of the embodiment. FIGS. 12 to 15 show examples of a waveform of the voltage ($V_{sig}$) supplied from the respiratory gas concentration detecting portion 100, and a respiratory waveform which is generated on the basis of the waveform of the voltage, in the measuring device 66.

In the measuring device 66 shown in FIG. 11, components similar to those of the measuring device 60 which has been described with reference to FIG. 4 or those of the measuring device 65 which has been described with reference to FIG. 9 are denoted by the same reference numerals, and their description is omitted. The waveforms indicated by "$CO_2$ CONCENTRATION" in FIGS. 12 to 15 are the respiratory waveform which is generated by the respiratory gas concentration calculating portion 210 on the basis of the voltage ($V_{sig}$) supplied from the respiratory gas concentration detecting portion 100.

The measuring device 66 has the respiratory gas concentration detecting portion 100 and a calculating processing portion 202, in the body unit 61. The calculating processing portion 202 includes a reserved water detecting portion 280 in addition to the components which are included by the calculating processing portion 200.

The reserved water detecting portion 280 receives the voltage ($V_{sig}$) supplied from the respiratory gas concentration detecting portion 100, and compares the value of the voltage ($V_{sig}$) with a preset attention arousing voltage ($V_{ALM1}$). In the example, the attention arousing voltage ($V_{ALM1}$) is set to a level at which the voltage ($V_{sig}$) is higher than the attention arousing voltage ($V_{ALM1}$) in the case where, in the use of the respiratory waveform analyzer 10, the measurement is performed without causing water to adhere to the transmissive windows 25 of the respiratory airway adaptor 20.

Figure 12:
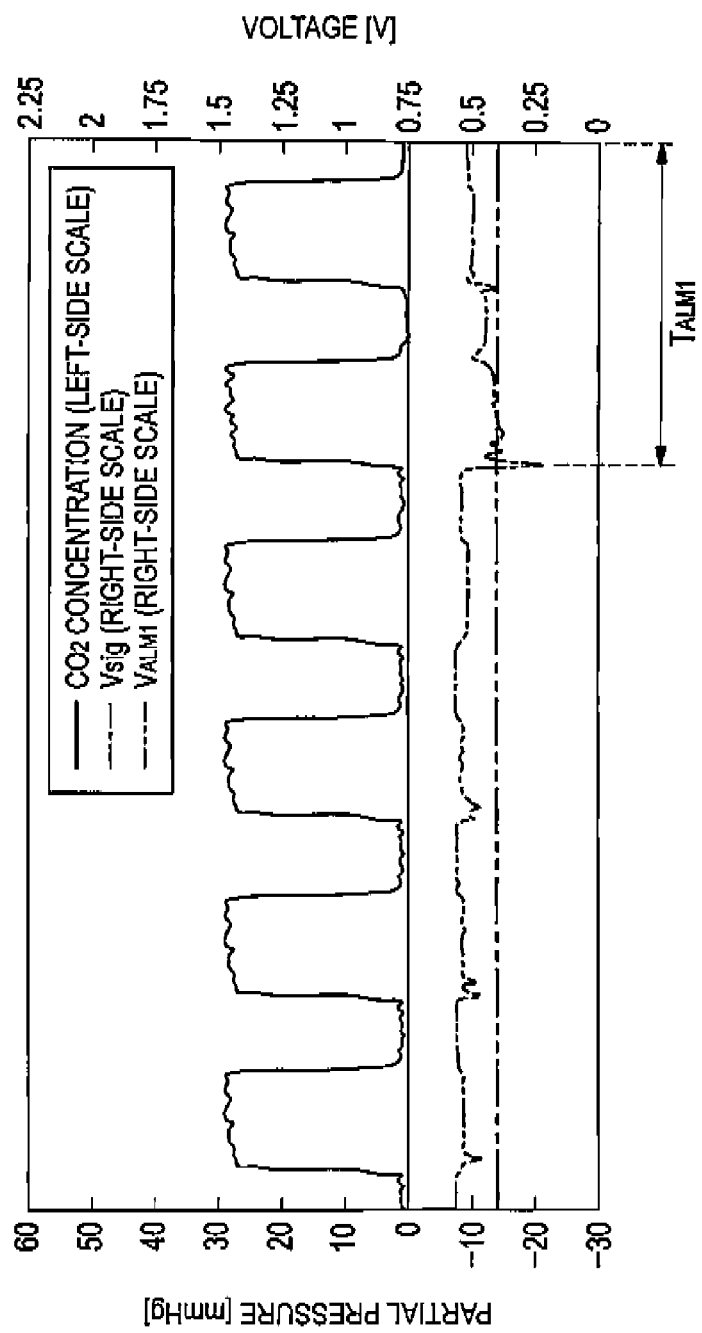
FIG. 12 is a view showing an example of a waveform of a voltage ($V_{sig}$) supplied from the respiratory gas concentration detecting portion, and a respiratory waveform which is generated on the basis of the waveform of the voltage, in the measuring device.

When, in the use of the respiratory waveform analyzer 10, water reserved in the respiratory airway adaptor 20 adheres to the transmissive windows 25 of the respiratory airway adaptor 20, the intensity of light received by the light receiver 53 of the sensor portion 50 is lowered. When the voltage ($V_{sig}$) is lowered in accordance with the lowering of the intensity of the light received by the light receiver 53, to be lower than the attention arousing voltage ($V_{ALM1}$) as shown in FIG. 12, the reserved water detecting portion 280 supplies an attention arousing signal indicative of a possibility that water is reserved in the respiratory airway adaptor 20, to the displaying portion 62. Upon receiving the attention arousing signal, the displaying portion 62 displays for a constant time period ($T_{ALM1}$) an attention arousing message indicating that water may be possibly reserved in the respiratory airway adaptor 20, based on the attention arousing signal.

When the voltage ($V_{sig}$) is lowered to be lower than the attention arousing voltage ($V_{ALM1}$), the reserved water detecting portion 280 compares the value of the voltage ($V_{sig}$) with a preset alarm voltage ($V_{ALM2}$). In the example, the alarm voltage ($V_{ALM2}$) is set to a level at which the voltage ($V_{sig}$) is lower than the alarm voltage ($V_{ALM2}$) in the case where, in the use of the respiratory waveform analyzer 10, the measurement is performed in a state where water adheres to a substantially whole face of the transmissive windows 25 of the respiratory airway adaptor 20.

Figure 13:
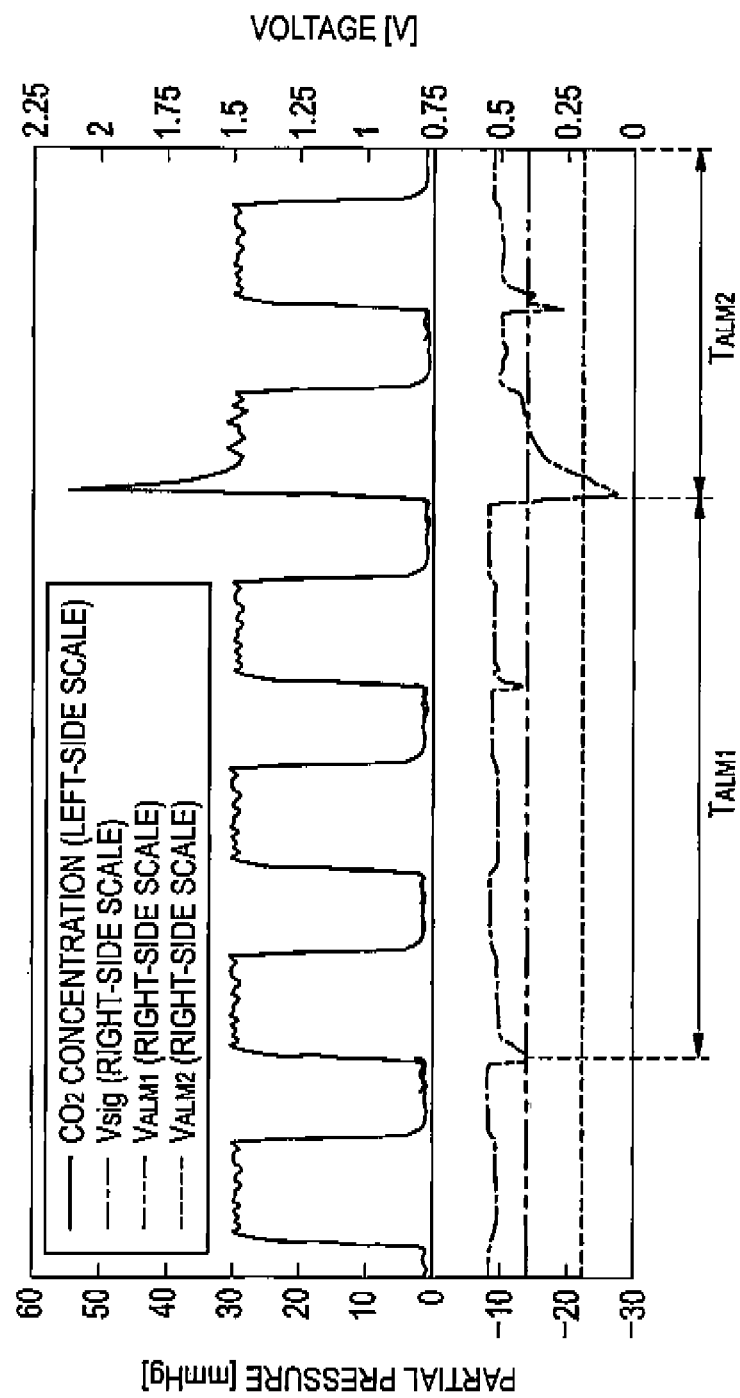
FIG. 13 is a view showing an example of the waveform of the voltage ($V_{sig}$) supplied from the respiratory gas concentration detecting portion, and the respiratory waveform which is generated on the basis of the waveform of the voltage, in the measuring device.

When the voltage ($V_{sig}$) is further lowered to be lower than the alarm voltage ($V_{ALM2}$) as shown in FIG. 13, the reserved water detecting portion 280 supplies an alarm signal indicating that water is reserved in the respiratory airway adaptor 20, to the displaying portion 62. Upon receiving the alarm signal, the displaying portion 62 displays for a constant time period ($T_{ALM2}$) an alarm message indicating, for example, that water is reserved in the respiratory airway adaptor 20, based on the alarm signal.

Figure 14:
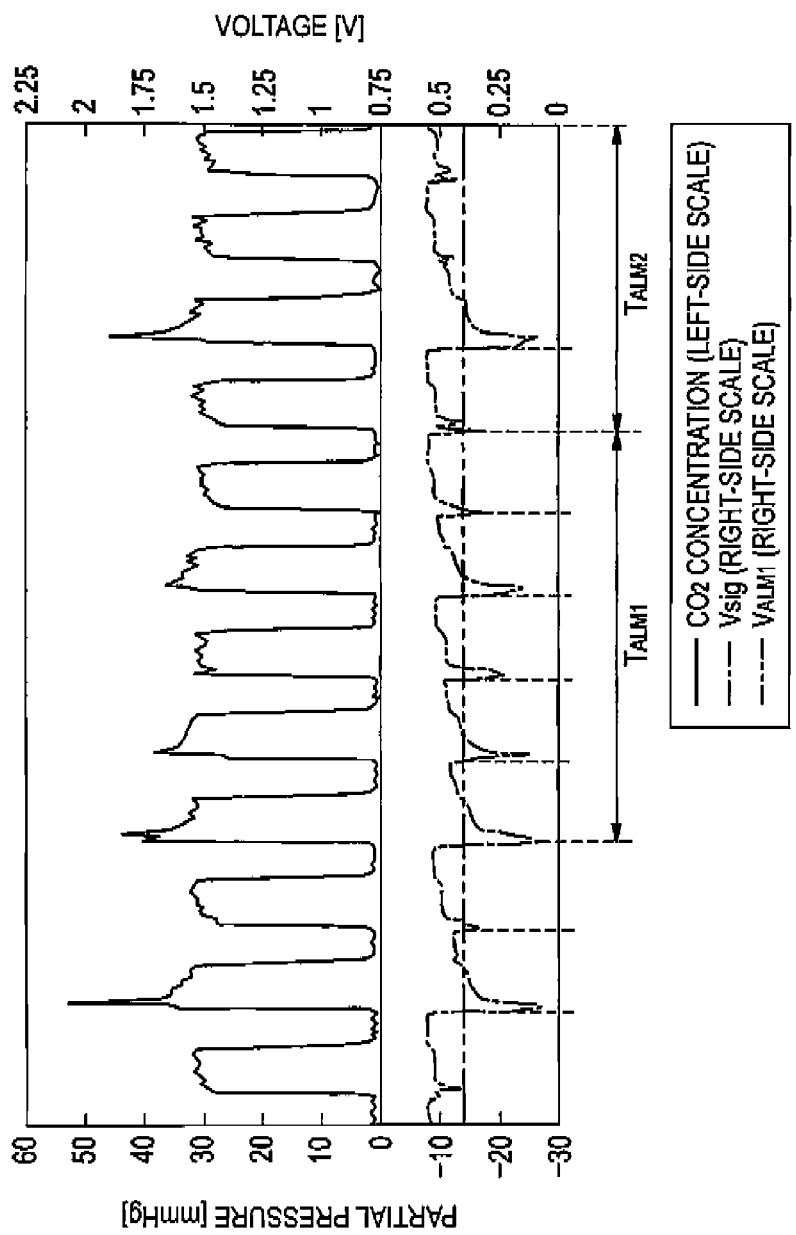
FIG. 14 is a view showing an example of the waveform of the voltage ($V_{sig}$) supplied from the respiratory gas concentration detecting portion, and the respiratory waveform which is generated on the basis of the waveform of the voltage, in the measuring device.

Furthermore, the reserved water detecting portion 280 may accumulate the number at which the value of the voltage ($V_{sig}$) is smaller than the preset attention arousing voltage ($V_{ALM1}$) as shown in FIG. 14, for each respiratory waveform, and, at a timing when the number of smaller values reaches a preset number (in FIG. 14, three), supply the attention arousing signal to the displaying portion 62.

Moreover, the reserved water detecting portion 280 may count the number at which the value of the voltage ($V_{sig}$) is smaller than the attention arousing voltage ($V_{ALM1}$), and, at a timing when the counted number reaches a preset number (in FIG. 14, eight) which is a number larger than the above-mentioned number, supply the alarm signal to the displaying portion 62.

Figure 15:
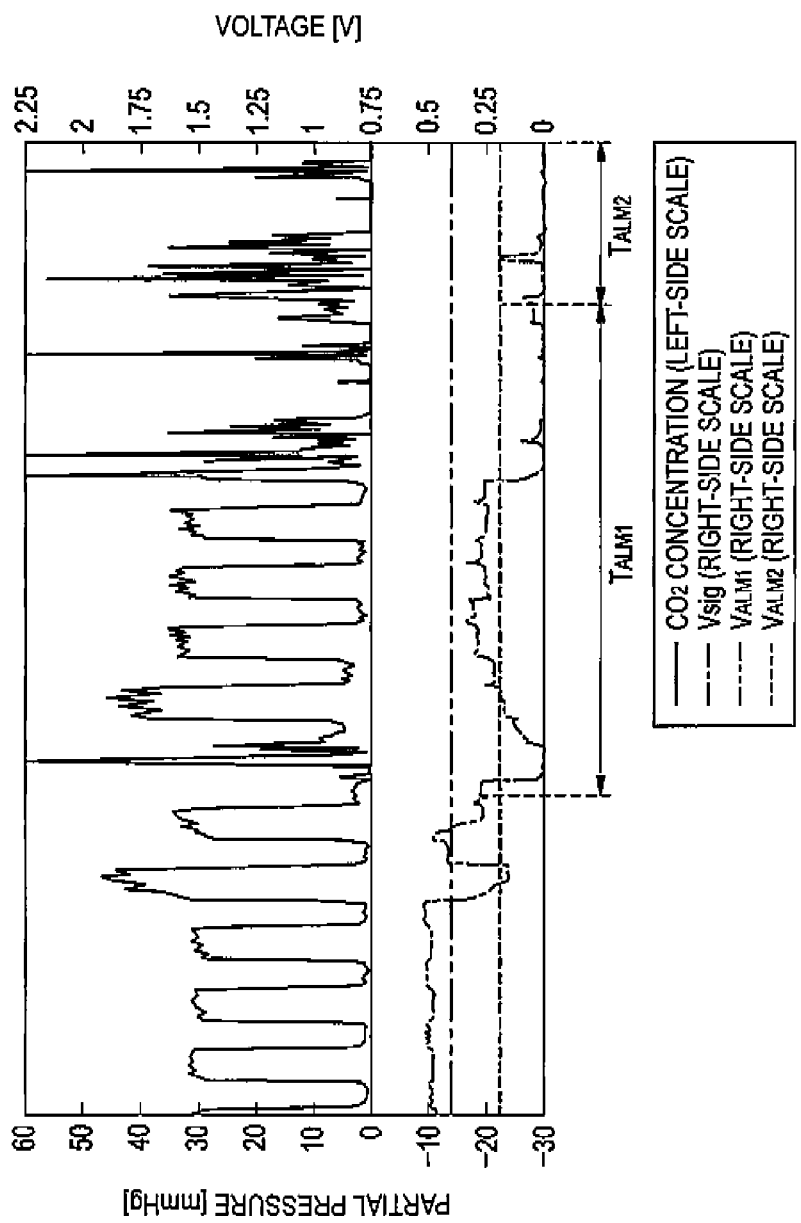
FIG. 15 is a view showing an example of the waveform of the voltage ($V_{sig}$) supplied from the respiratory gas concentration detecting portion, and the respiratory waveform which is generated on the basis of the waveform of the voltage, in the measuring device.

Furthermore, the reserved water detecting portion 280 may accumulate the time period during which the value of the voltage ($V_{sig}$) is smaller than the preset attention arousing voltage ($V_{ALM1}$) as shown in FIG. 15, and, at a timing when the accumulated time period reaches a preset time period, supply the attention arousing signal to the displaying portion 62. Moreover, the reserved water detecting portion 280 may accumulate the time period during which the value of the voltage ($V_{sig}$) is smaller than the preset alarm voltage ($V_{ALM2}$) as shown in FIG. 15, and, at a timing when the accumulated time period reaches a preset time period, supply the alarm signal to the displaying portion 62.

As described above, the respiratory waveform analyzer 10 of the embodiment further includes the reserved water detecting portion 280, and hence can detect that water is reserved in the respiratory airway adaptor 20, to perform an attention arousal and an alarm to the user of the apparatus. In the example, the attention arousal and alarm related to reserving of water in the respiratory airway adaptor 20 are performed by means of a message display on the displaying portion 62. Alternatively, the attention arousal and the alarm may be performed by means of, for example, a buzzer or an audio assist.

In the above-described embodiment example of the respiratory waveform analyzer 10, the light emitter 52 emits light (signal light) of a band in which the rate of absorption by $CO_2$ gas is high, and the light receiver 53 receives the light which has undergone absorption in accordance with the concentration of $CO_2$ contained in the respiration. Hereinafter, an embodiment example in which the light emitter 52 emits also light (referential light) of a band in which the rate of absorption by $CO_2$ gas is low, in addition to the signal light will be described. The respiratory waveform analyzer 10 which will be described below has a configuration similar to that of the respiratory waveform analyzer 10 of the above-described embodiment example.

In the example, the light emitter 52 alternately emits the signal light and the referential light. The respiratory gas concentration detecting portion 100 outputs voltages of levels which correspond to the receiving intensities of the signal light and the referential light, respectively. In the example, namely, the respiratory gas concentration detecting portion 100 outputs the voltage ($V_{sig}$) of a level which corresponds to the receiving intensity of the signal light, and also a voltage ($V_{ref}$) of a level which corresponds to the receiving intensity of the referential light. Since the referential light is not substantially absorbed by $CO_2$ as compared with the signal light, the value of the voltage ($V_{ref}$) is changed by increasing and decreasing of the concentration of $CO_2$ contained in the respiration, in a less degree as compared with the voltage ($V_{sig}$). In order to alternately emit the signal light and the referential light, a plurality of light sources for emitting light may be provided respectively as the light emitter 52. In addition, the configuration may be used in which a single light source for emitting light having a large band is provided as the light emitter 52, the light from the single light source is divided at the light receiver 53 and the signal light and the referential light are generated by using filters, which have different characteristics, for filtering the divided light.

With respect to the receiving intensity of the referential light, the following expression holds in accordance with the Lambert-Beer Law.

$$\text{ref}/\text{ref0} = e^{-ECD} \quad [\text{Exp. 4}]$$

In expression (Exp. 4) above, ref indicates the receiving intensity of the referential light, and ref0 indicates the receiving intensity of the referential light (standard referential light) in a state where no water is reserved in the respiratory airway adaptor 20. Furthermore, E indicates the absorption coefficient, C indicates the concentration of water existing in the optical path of the referential light, and D indicates the thickness of the water in the direction of the optical path. Moreover, above expression (Exp. 4) can be transformed in the following manner.

$$ECD = -\ln(\text{ref}/\text{ref0}) \quad [\text{Exp. 5}]$$

In the expression, the absorption coefficient (E) of the water reserved in the respiratory airway adaptor 20, and the concentration (C) of the water can be regarded as constants, and hence above expression (Exp. 5) is an expression showing the relationship between the quantity of water reserved in the respiratory airway adaptor 20 and the degree of attenuation of the referential light caused by the water (the attenuance due to water). When the voltage which is output by the respiratory gas concentration detecting portion 100 on the basis of the receiving intensity of the standard referential light is indicated by $V_{ref0}$, ref/ref0 can be approximated by $V_{ref}/V_{ref0}$.

In the respiratory waveform analyzer 10 of the example, the reserved water detecting portion 280 stores expression (Exp. 5) above, and the components of expression (Exp. 5) above, i.e., the absorption coefficient (E), the concentration (C), and the voltage ($V_{ref0}$) corresponding to the receiving intensity of the standard referential light are preset. In the example, the voltage ($V_{ref0}$) corresponding to the receiving intensity of the standard referential light may be obtained by actual measurement, or alternatively may be obtained, for example, in the following manner on the basis of $V_{ref}$ and the ratio ($V_{sig}/V_{ref}$) of $V_{sig}$ and $V_{ref}$.

Figure 16:
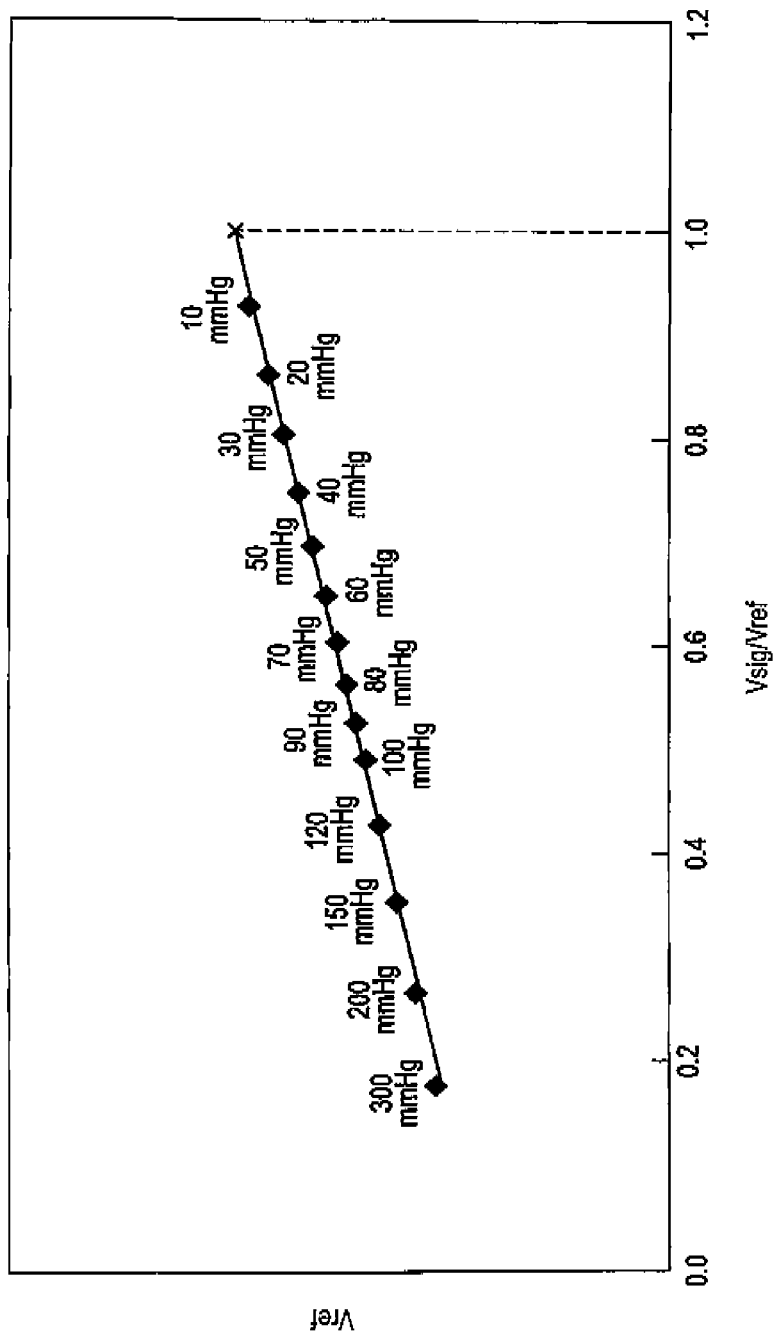
FIG. 16 is a view showing relationships between $V_{ref}$ and $V_{sig}/V_{ref}$ due to a change of a $CO_2$ concentration of the respiration.

FIG. 16 shows relationships between $V_{ref}$ and $V_{sig}/V_{ref}$ due to a change of the $CO_2$ concentration of the respiratory. Each of the plots shown in FIG. 16 shows the relationship between $V_{ref}$ and $V_{sig}/V_{ref}$ at the $CO_2$ concentration indicated in the vicinity of the plot. The straight line shown in FIG. 16 shows a linear approximation of the plots.

As shown in FIG. 16, the value of the voltage ($V_{ref0}$) corresponding to the receiving intensity of the referential light (standard referential light) in a state where no water is reserved in the respiratory airway adaptor 20 can be approximately obtained by the value of $V_{ref}$ in the case where $V_{sig}/V_{ref}$ is 1.0 on the straight line obtained by the linear approximation of the plots (the value of $V_{ref}$ at the plot indicated by "x" in FIG. 16).

Figure 17:
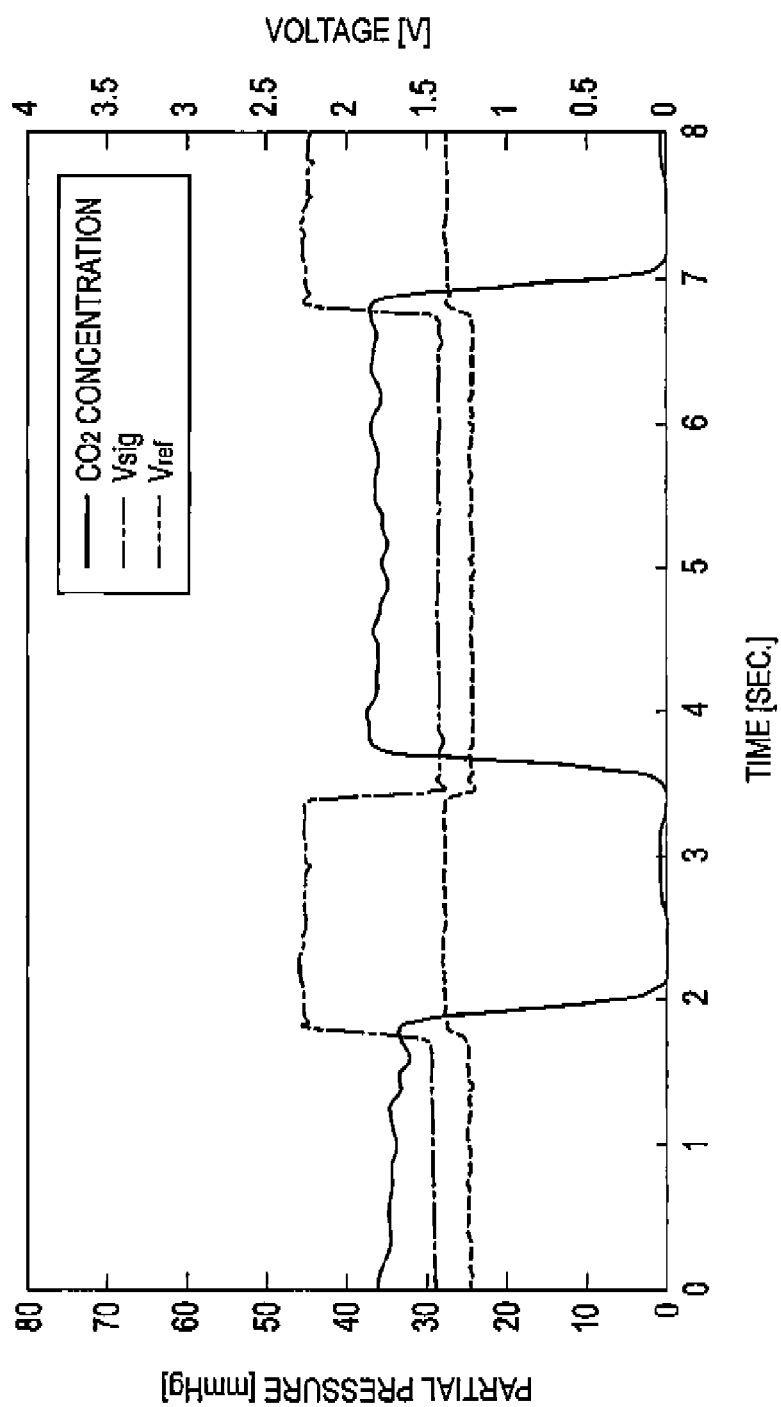
FIG. 17 is a view showing an example of waveforms of $V_{sig}$, $V_{ref}$, and a $CO_2$ concentration which is generated on the basis of $V_{sig}$, in a state where water is not reserved in optical paths of signal light and referential light inside the respiratory airway adaptor.
Figure 18:
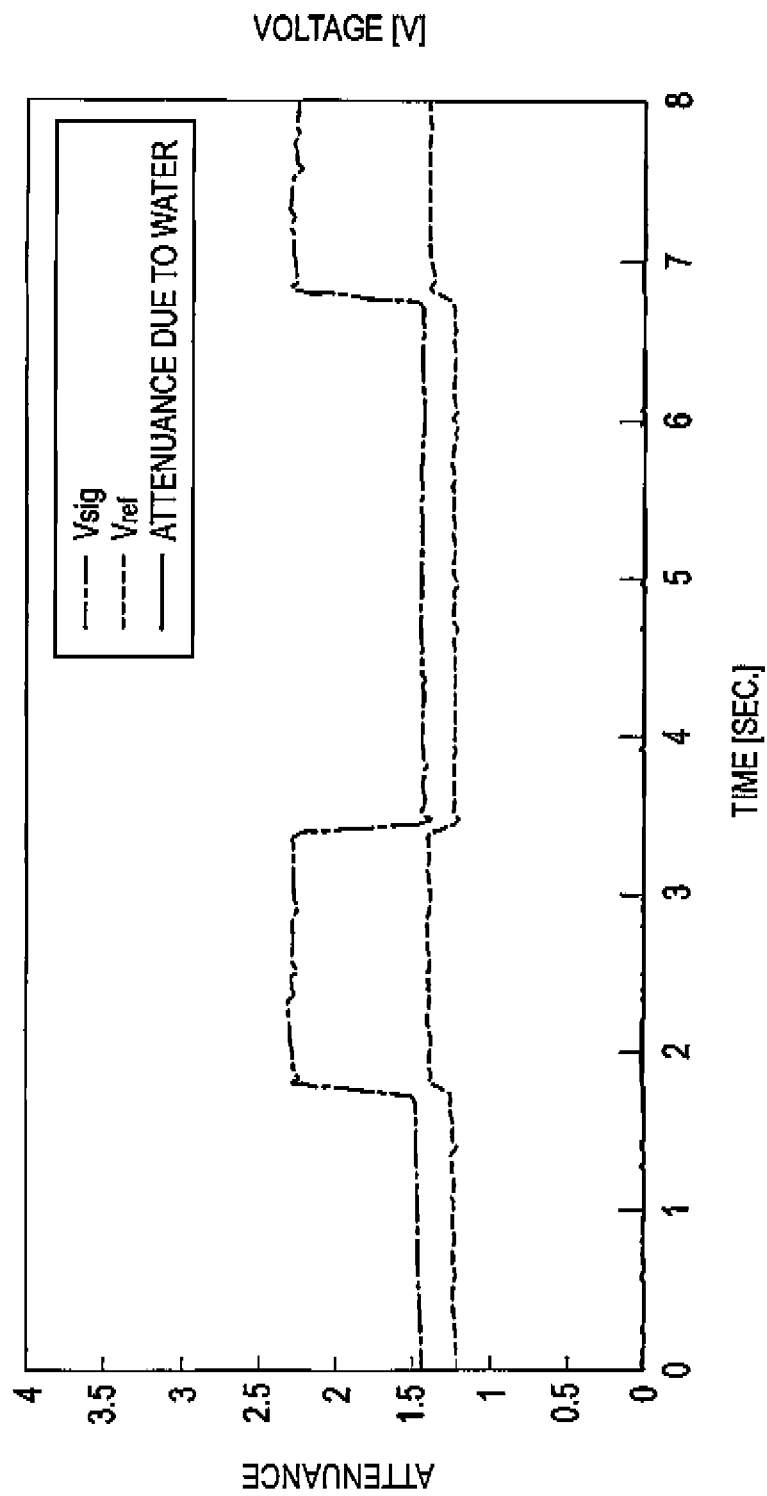
FIG. 18 is a view showing relationships between the waveforms of $V_{sig}$ and $V_{ref}$ and the attenuance due to water which is reserved in the respiratory airway adaptor, in the state where water is not reserved in the optical paths of the signal light and the referential light inside the respiratory airway adaptor.

FIG. 17 shows an example of waveforms of $V_{sig}$, $V_{ref}$, and the $CO_2$ concentration which is generated on the basis of $V_{sig}$, in the state where water is not reserved in the optical paths of the signal light and the referential light inside the respiratory airway adaptor 20, and FIG. 18 shows relationships between the waveforms of $V_{sig}$ and $V_{ref}$, and the attenuance due to water which is reserved in the respiratory airway adaptor 20, in the state.

Figure 19:
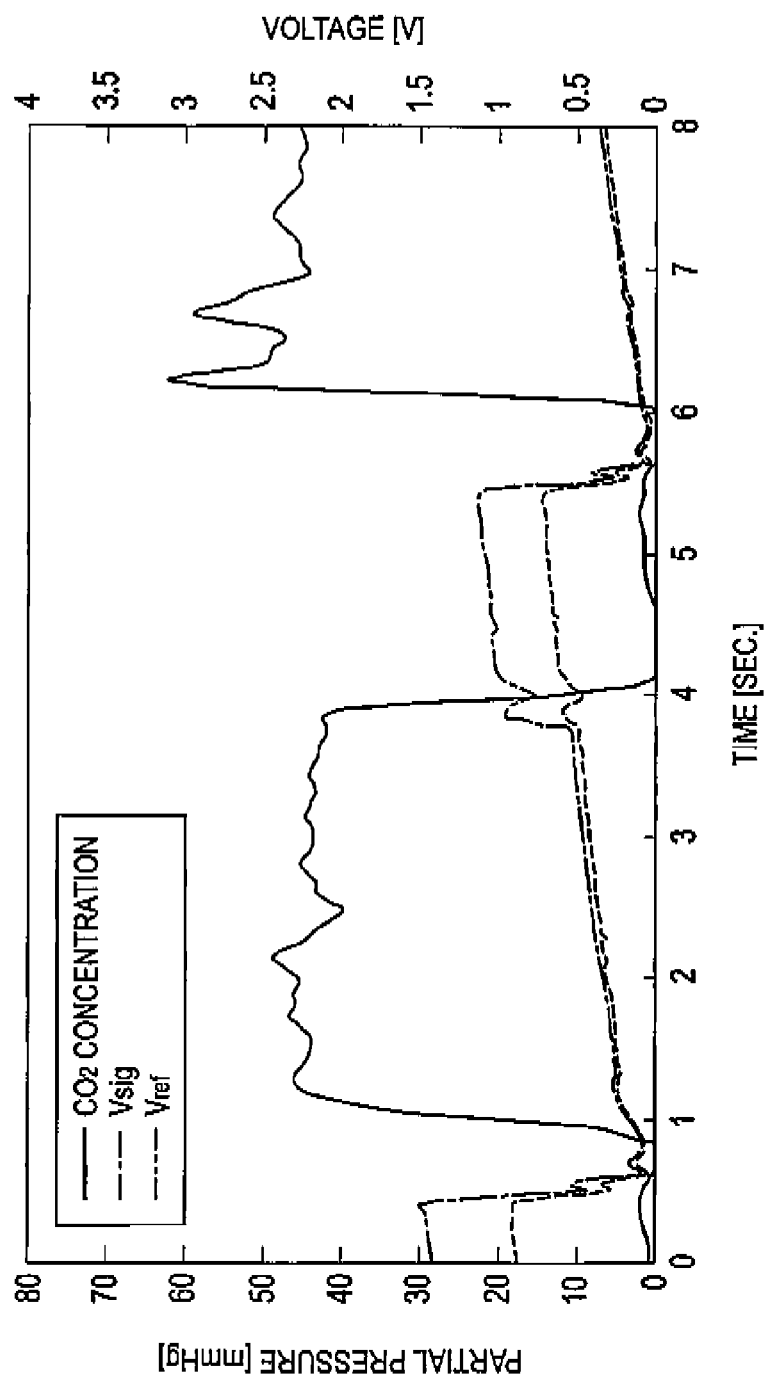
FIG. 19 is a view showing an example of waveforms of $V_{sig}$, $V_{ref}$, and a $CO_2$ concentration which is generated on the basis of $V_{sig}$, in a state where water is reserved in the optical paths of the signal light and the referential light inside the respiratory airway adaptor.
Figure 20:
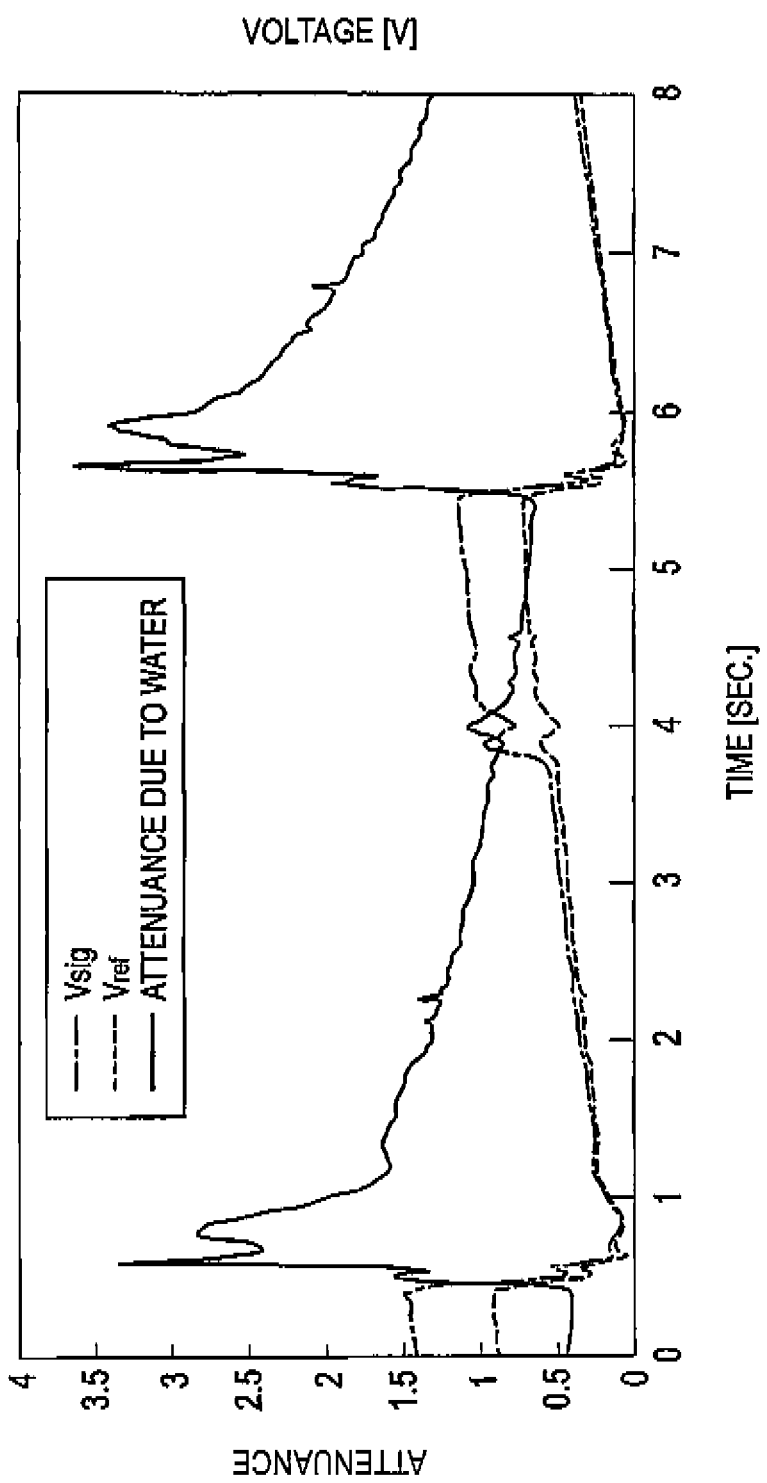
FIG. 20 is a view showing relationships between the waveforms of $V_{sig}$ and $V_{ref}$, and the attenuance due to water which is reserved in the respiratory airway adaptor, in the state where water is reserved in the optical paths of the signal light and the referential light inside the respiratory airway adaptor.

FIG. 19 shows an example of waveforms of $V_{sig}$, $V_{ref}$, and the $CO_2$ concentration which is generated on the basis of $V_{sig}$, in the state where water is reserved in the optical paths of the signal light and the referential light inside the respiratory airway adaptor 20, and FIG. 20 shows relationships between the waveforms of $V_{sig}$ and $V_{ref}$, and the attenuance due to water which is reserved in the respiratory airway adaptor 20, in the state.

As shown in FIGS. 17 and 18, in the state, where water is not reserved in the optical paths of the signal light and the referential light inside the respiratory airway adaptor 20, even when the voltage ($V_{ref}$) corresponding to the receiving intensity of the referential light, and the voltage ($V_{sig}$) corresponding to the receiving intensity of the signal light are varied by a change of the concentration of $CO_2$ contained in the respiration of the subject, the attenuance (ECD in Exp. 5) is approximately 0.

As shown in FIGS. 19 and 20, by contrast, when water is reserved in the respiratory airway adaptor 20 to cover at least a part of the optical paths of the signal light and the referential light, both the referential light and the signal light are attenuated. At this time, the attenuance (ECD in Exp. 5) is increased in accordance with the degrees of the attenuances of the referential light and the signal light. Therefore, the attenuance (ECD in Exp. 5) is more increased as the quantity of water reserved in the respiratory airway adaptor 20 is larger.

In the respiratory waveform analyzer 10 of the example, the reserved water detecting portion 280 calculates the attenuance (ECD in Exp. 5) showing such a tendency, and, based on the value of the tendency, can detect the quantity of water reserved in the respiratory airway adaptor 20. In the above described embodiment, the object for the detection is described as the water. However, the respiratory waveform analyzer 10 according to an aspect of the above embodiment can detect a material, for example a liquid, other than the water.

Although the invention has been described using the embodiment, the technical scope of the invention is not restricted to the scope of the description of the embodiment. It is obvious to those skilled in the art that various changes or improvements can be made on the embodiment. It is obvious from the definition of the appended claims that also embodiments in which such changes or improvements are made belong to the technical scope of the invention.

Although the respiratory waveform analyzer 10 is an apparatus for measuring the $CO_2$ concentration in the respiration of the subject, for example, the invention is not restricted to an apparatus for measuring a specific component in the respiration of the subject. For example, an apparatus for measuring one or more components in the expiration or inspiration of the subject belongs to the technical scope of the invention.

According to an aspect of the invention, when the concentration of a component in the respiratory gas of the subject is detected and the respiratory waveform on the basis of a temporal change of the concentration is analyzed, the reliability of the respiratory waveform is referred, and therefore it is possible to correctly know noise components in the respiratory waveform.

According to an aspect of the invention, when the effective concentration of the component in each respiration cycle is detected from the respiratory waveform, the use of the reliability causes a peak of noise components contained in the waveform corresponding to each respiration cycle, not to be falsely detected as the effective concentration.

According to an aspect of the invention, when a value (average value) which is obtained by averaging effective concentrations of waveforms corresponding to respiration cycles is to be calculated, the averaging is performed after the effective concentrations are weighted in accordance with the degree of the accumulated values of the reliabilities in the waveforms. Therefore, the effect of the noise components contained in the waveforms against the calculated average value (weighted average value) can be reduced.

According to an aspect of the invention, when the respiratory gas signal indicative of the concentration of the component has a specified value or greater, the effective concentration detecting portion detects the effective concentration during the concentration detecting time period. Therefore, the following effect is attained. Even in the case where, when the concentration of the component in the respiratory gas is measured by using the IR spectroscopy, water droplets or the like are attached to a light irradiation portion or detection portion for the expiration, and the level of the output signal from the detection portion is lowered, the detection is not affected by the level lowering of the output signal due to such an error cause, and hence it is possible to detect more correctly the effective concentration.

According to an aspect of the invention, the apparatus includes the concentration detection value correcting portion which corrects the respiratory waveform signal corresponding to the respiratory gas signal, in accordance with the ratio of the respiratory gas signal to the predetermined reference value. Even when a measurement involving the error cause is performed, therefore, an effect caused by the level lowering of the output signal can be reduced. Even in the case where the concentration signal is largely varied in one respiration cycle by the error cause, consequently, it is possible to prevent determination that a plurality of respirations are conducted, from being performed based on the waveform (the respiratory waveform signal) due to the concentration signal. Further, since the apparatus includes the reserved water detecting portion, it is possible to detect the water in the respiratory airway adaptor and to perform an attention arousal and an alarm to the user of the apparatus.

What is claimed is:

1. An expiratory waveform analyzer, operable to analyze an expiratory waveform, which is generated based on a concentration of a component in expiratory gas of a subject measured over a plurality of time intervals, the expiratory waveform analyzer comprising:
   an expiratory gas concentration generator which generates a concentration signal indicating values of the concentration of the component based on an output signal from a sensor that measures the concentration of the component;
   a flatness calculator which calculates differences between the values of the concentration of the component indicated by the concentration signal over the plurality of time intervals of the expiratory waveform based on the concentration signal, and which calculates a flatness of the expiratory waveform based on the calculated differences;
   a reliability calculator which calculates a reliability of the expiratory waveform based on the flatness and the values of the concentration of the component indicated by the concentration signal; and
   a respiratory rate detecting portion which determines whether the expiratory waveform is reliable for inclusion in calculation of a respiratory rate of the subject based on the reliability of the expiratory waveform, and calculates the respiratory rate of the subject using the expiratory waveform in response to determining that the expiratory waveform is reliable and calculates the respiratory rate of the subject without inclusion of the expiratory waveform in response to determining that the expiratory waveform is not reliable.

2. The expiratory waveform analyzer according to claim 1, wherein the flatness is a function of an accumulated value which is obtained by accumulating differences between the concentration of the component at time intervals during which the concentration of the component generating the expiratory waveform is measured by the sensor, based on the concentration signal.

3. The expiratory waveform analyzer according to claim 2, wherein the flatness is a function of absolute values of the differences.

4. The expiratory waveform analyzer according to claim 2, wherein the flatness is equal to:

$$\frac{1}{\{\Sigma(D\Delta tCO2)^2 + 1\}}$$

wherein D$\Delta$tCO2 is a difference between a current $CO_2$ concentration and a previous $CO_2$ concentration at time interval $\Delta t$.

5. The expiratory waveform analyzer according to claim 1, wherein the reliability calculator calculates the reliability based on the flatness which is calculated at a timing by the flatness calculator, and the values of the concentration of the component indicated by the concentration signal at the timing.

6. The expiratory waveform analyzer according to claim 5, further comprising:
an effective concentration detector which detects a value of the concentration signal at a timing when the reliability that is calculated in a predetermined concentration detecting time period is maximum, as an effective concentration of the component in the expiratory gas in the concentration detecting time period.

7. The expiratory waveform analyzer according to claim 6, wherein the effective concentration detector accumulates the reliability in the concentration detecting time period to obtain an accumulated value in the concentration detecting time period, determines whether the expiratory waveform is reliable for inclusion in calculation of the effective concentration of the component in the expiratory gas of the subject based on whether the reliability in the concentration detecting time period exceeds a predetermined reliability, detects the effective concentration in the concentration detecting time period in response to determining that the expiratory waveform is reliable for inclusion in calculation of the effective concentration of the component in the expiratory gas of the subject and does not detect the effective concentration in the detecting time period in response to determining that the expiratory waveform is not reliable for inclusion in calculation of the effective concentration of the component in the expiratory gas of the subject, and calculates the effective concentration of the component in the expiratory gas of the subject, using the expiratory waveform if the expiratory waveform is reliable for inclusion in calculation of the effective concentration of the component in the expiratory gas of the subject and calculates the effective concentration of the component in the expiratory gas of the subject without inclusion of the expiratory waveform if the expiratory waveform is not reliable for inclusion in calculation of the effective concentration of the component in the expiratory gas of the subject.

8. The expiratory waveform analyzer according to claim 7, wherein the concentration detecting time period is a time period corresponding to one cycle of the expiratory waveform.

9. The expiratory waveform analyzer according to claim 8, further comprising:
a weighted average processor which, when a plurality of the effective concentrations are detected, weights each of the effective concentrations in accordance with degree of the accumulated value in the corresponding concentration detecting time period, and averages the weighted effective concentrations, to calculate a weighted average value.

10. The expiratory waveform analyzer according to claim 9, further comprising:
a display that displays at least one of a number at which the effective concentration detector detects the effective concentration in a time period, and the weighted average value calculated by the weighted average processor.

11. The expiratory waveform analyzer according to claim 6, wherein the expiratory gas concentration generator includes:
an expiratory gas concentration detector which converts an analog signal output from the sensor to a digital expiratory gas signal; and
an expiratory gas concentration calculator which generates the expiratory waveform signal based on the expiratory gas signal from the expiratory gas concentration detector,
the concentration signal is the expiratory waveform signal, and
when a value of the expiratory gas signal is a value or greater, which indicates that the concentration of the component is high, the effective concentration detector detects the effective concentration in the concentration detecting time period.

12. The expiratory waveform analyzer according to claim 11, further comprising:
a concentration detection value corrector which corrects the expiratory waveform signal corresponding to the expiratory gas signal, in accordance with a ratio of the expiratory gas signal to a predetermined reference value.

13. The expiratory waveform analyzer according to claim 1, further comprising:
an expiratory airway adaptor in which the expiratory gas of the subject flows; and
a liquid detector which detects a liquid in the expiratory airway adaptor.

14. The expiratory waveform analyzer of claim 1, wherein the reliability of the expiratory waveform indicates one of (i) to include the expiratory waveform in a determination of an expiratory rate of the subject and (ii) to ignore the expiratory waveform in the determination of the expiratory rate of the subject.

15. An expiratory waveform analyzer comprising:
a sensor that detects over a duration of time a concentration of a gas component of a subject at each of a plurality of time intervals in the duration of time;
an expiratory gas concentration generator that generates an expiratory waveform over the duration of time based on the concentration of the gas component at each of the plurality of time intervals;
a flatness calculating portion that calculates differences between the concentration of the gas component at each consecutive pair of the plurality of time intervals in the duration of time, and that calculates a flatness scaling factor for each of the plurality of time intervals based on the calculated differences;

a reliability calculating portion that scales the concentration of the gas component at each of the plurality of time intervals by the flatness scaling factor for the respective each of the plurality of time intervals, the scaled concentration of the gas component at each of the plurality of time intervals being a reliability of the concentration of the gas component at each of the plurality of time intervals;

an effective concentration detecting portion that determines a reliability of the expiratory waveform based on the reliabilities of the concentration of the gas component at each of the plurality of time intervals, compares the reliability of the expiratory waveform to a waveform reliability threshold, and determines whether the expiratory waveform is a reliable expiratory waveform based on a result of the comparing; and an expiratory rate detecting portion that calculates an expiratory rate of the patient based on the expiratory waveform in response to the effective concentration detecting portion determining that the expiratory waveform is the reliable expiratory waveform, wherein the expiratory rate detecting portion calculates the expiratory rate of the patient by ignoring the expiratory waveform in response to the effective concentration detecting portion determining that the expiratory waveform is not the reliable expiratory waveform.

* * * * *